(12) United States Patent
Nilsson et al.

(10) Patent No.: US 8,906,420 B2
(45) Date of Patent: Dec. 9, 2014

(54) PHARMACEUTICAL FORMULATION COMPRISING ONE OR MORE FUMARIC ACID ESTERS IN AN EROSION MATRIX

(75) Inventors: Henrik Nilsson, Feusisberg (CH); Roland Rupp, Bergisch Gladbach (DE)

(73) Assignee: Forward Pharma A/S, Copenhagen K (DK)

( * ) Notice: Subject to any disclaimer, the term of this patent is extended or adjusted under 35 U.S.C. 154(b) by 0 days.

(21) Appl. No.: 13/143,498

(22) PCT Filed: Jan. 8, 2010

(86) PCT No.: PCT/EP2010/050172
§ 371 (c)(1),
(2), (4) Date: Oct. 26, 2011

(87) PCT Pub. No.: WO2010/079222
PCT Pub. Date: Jul. 15, 2010

(65) Prior Publication Data
US 2012/0034303 A1    Feb. 9, 2012

Related U.S. Application Data

(60) Provisional application No. 61/143,613, filed on Jan. 9, 2009.

(30) Foreign Application Priority Data

Jan. 9, 2009   (DK) .................................. 2009 00034

(51) Int. Cl.
| A61K 9/16 | (2006.01) |
| A61K 9/20 | (2006.01) |
| A61K 9/28 | (2006.01) |
| A61K 31/225 | (2006.01) |
| A61K 31/215 | (2006.01) |

(52) U.S. Cl.
CPC ............. A61K 9/2866 (2013.01); A61K 9/2054 (2013.01); A61K 9/2886 (2013.01); A61K 31/225 (2013.01); A61K 31/215 (2013.01); A61K 9/2846 (2013.01)
USPC ............................ 424/490; 424/474; 424/464

(58) Field of Classification Search
None
See application file for complete search history.

(56) References Cited

U.S. PATENT DOCUMENTS

| 4,145,438 | A | | 3/1979 | Kingsley et al. |
| 4,302,440 | A | | 11/1981 | John et al. |
| 4,693,896 | A | * | 9/1987 | Wheatley et al. ............. 424/480 |
| 4,851,439 | A | | 7/1989 | Speiser et al. |
| 4,911,917 | A | | 3/1990 | Kuhrts |
| 4,959,389 | A | | 9/1990 | Speiser et al. |
| 5,023,245 | A | | 6/1991 | Kuhrts |
| 5,149,695 | A | | 9/1992 | Speiser et al. |
| 5,214,196 | A | | 5/1993 | Blank |
| 5,242,905 | A | | 9/1993 | Blank |
| 5,424,332 | A | | 6/1995 | Speiser et al. |
| 5,451,667 | A | | 9/1995 | Speiser et al. |
| 5,484,610 | A | | 1/1996 | Bae |
| 5,589,504 | A | | 12/1996 | Dannenberg et al. |
| 5,681,584 | A | | 10/1997 | Savastano et al. |
| 5,716,625 | A | | 2/1998 | Hahn et al. |
| 5,804,203 | A | | 9/1998 | Hahn et al. |
| 5,851,556 | A | | 12/1998 | Breton et al. |
| 5,856,356 | A | | 1/1999 | Tsouderos et al. |
| 6,139,850 | A | | 10/2000 | Hahn et al. |
| 6,277,882 | B1 | | 8/2001 | Joshi et al. |
| 6,287,599 | B1 | | 9/2001 | Burnside et al. |
| 6,355,676 | B1 | | 3/2002 | Joshi et al. |
| 6,359,003 | B1 | | 3/2002 | Joshi et al. |
| 6,436,992 | B1 | | 8/2002 | Joshi et al. |
| 6,509,376 | B1 | | 1/2003 | Joshi et al. |
| 6,537,584 | B1 | | 3/2003 | Zentner et al. |
| 6,613,800 | B1 | | 9/2003 | Smith |
| 6,730,693 | B2 | | 5/2004 | Buononato |
| 6,812,248 | B2 | | 11/2004 | Zhang et al. |
| 6,858,750 | B2 | | 2/2005 | Joshi et al. |
| 7,157,423 | B2 | | 1/2007 | Joshi et al. |
| 7,320,999 | B2 | | 1/2008 | Joshi et al. |
| 7,432,240 | B2 | | 10/2008 | Joshi et al. |
| 7,498,044 | B2 | | 3/2009 | Petereit et al. |
| 7,612,110 | B2 | | 11/2009 | Joshi et al. |
| 7,619,001 | B2 | | 11/2009 | Joshi et al. |
| 7,790,916 | B2 | | 9/2010 | Joshi et al. |
| 7,803,840 | B2 | | 9/2010 | Joshi et al. |
| 7,906,659 | B2 | | 3/2011 | Joshi et al. |
| 7,915,310 | B2 | | 3/2011 | Joshi et al. |

(Continued)

FOREIGN PATENT DOCUMENTS

| CN | 1433303 A | 7/2003 |
| CN | 1487828 A | 4/2004 |

(Continued)

OTHER PUBLICATIONS

English Language Translation of the First Office Action issued in Chinese Patent Application No. 201080011787.1, issued Dec. 3, 2012 (24 pages).
Agarwal et al., "[P07.102] Effects of BG-12 on quality of life in patients with relapsing-remitting multiple sclerosis: Findings from the DEFINE study," Neurology 78:P07.102 (2012).
Albrecht et al., "[P02.120] Dimethylfumarate protects from oxidative stress by increasing glutathione," Neurology 78:P02.120 (2012).
Altmeyer et al., "Antipsoriatic effect of fumaric acid derivatives: Results of a multicenter double-blind study in 100 patients," J. Am. Acad. Dermatol. 30:977-981 (1994).
Anon., "BG 12: BG 00012, BG 12/Oral Fumarate, FAG-201, second-generation fumarate derivative—Fumapharm/Biogen Idec," Drugs R D 6:229-230 (2005).
Anon., "Handbook of Pharmaceutical Excipients" entry for Ethylcellulose, translated into Japanese by the Pharmaceutical Society of Japan, pp. 44-47 (1989).

(Continued)

Primary Examiner — Michael G Hartley
Assistant Examiner — Robert Cabral
(74) Attorney, Agent, or Firm — Clark & Elbing LLP

(57) ABSTRACT

A pharmaceutical formulation comprising an erosion matrix comprising one or more fumaric acid esters as well as one or more rate-controlling agents, wherein erosion of said erosion matrix permits controlled release of said fumaric acid ester(s).

21 Claims, 1 Drawing Sheet

(56) References Cited

U.S. PATENT DOCUMENTS

Figure 1:
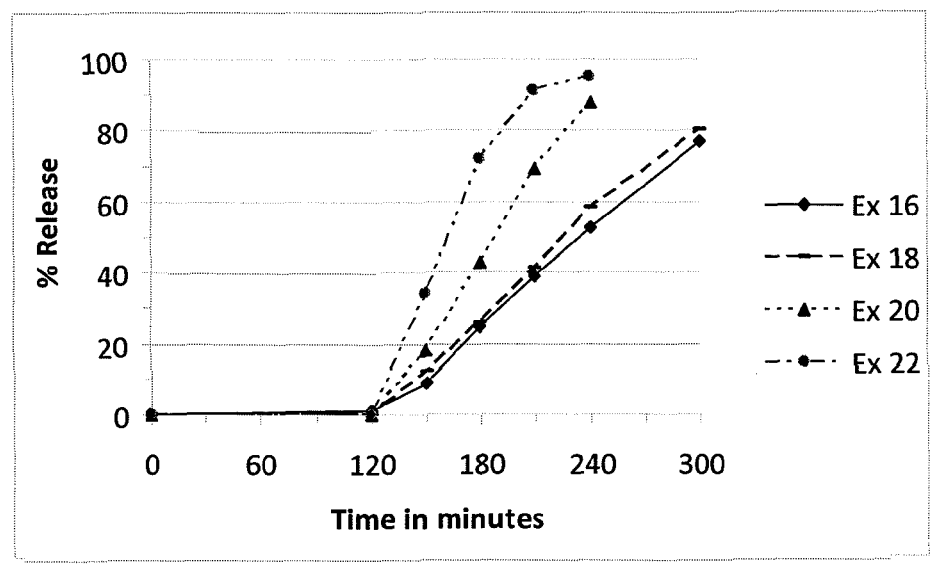

| | | |
|---|---|---|
| 8,147,871 B2 | 4/2012 | Brown et al. |
| 8,148,414 B2 | 4/2012 | Gangakhedkar et al. |
| 2002/0016369 A1 | 2/2002 | Villa et al. |
| 2003/0013761 A1 | 1/2003 | Joshi et al. |
| 2003/0018072 A1 | 1/2003 | Joshi et al. |
| 2003/0152622 A1 | 8/2003 | Louie-Helm et al. |
| 2004/0002544 A1 | 1/2004 | Makino et al. |
| 2004/0038889 A1 | 2/2004 | Joshi et al. |
| 2004/0054001 A1 | 3/2004 | Joshi et al. |
| 2004/0062800 A1 | 4/2004 | Burnside et al. |
| 2005/0152977 A1 | 7/2005 | Petereit et al. |
| 2005/0220878 A1 | 10/2005 | Fegely et al. |
| 2005/0220909 A1 | 10/2005 | Theoharides |
| 2005/0249807 A1 | 11/2005 | Brown et al. |
| 2007/0027076 A1 | 2/2007 | Joshi et al. |
| 2007/0178156 A1 | 8/2007 | Brown et al. |
| 2007/0248662 A1 | 10/2007 | Joshi et al. |
| 2007/0248663 A1 | 10/2007 | Joshi et al. |
| 2008/0004344 A1 | 1/2008 | Nilsson et al. |
| 2008/0227847 A1 | 9/2008 | Nilsson et al. |
| 2008/0233185 A1 | 9/2008 | Joshi et al. |
| 2008/0274182 A1 | 11/2008 | Alida Boekema et al. |
| 2008/0299196 A1 | 12/2008 | Nilsson et al. |
| 2008/0300217 A1 | 12/2008 | Nilsson |
| 2009/0110728 A1 | 4/2009 | Rastogi et al. |
| 2009/0181085 A1 | 7/2009 | Joshi et al. |
| 2009/0182047 A1 | 7/2009 | Joshi et al. |
| 2009/0215145 A1 | 8/2009 | Park et al. |
| 2009/0304790 A1 | 12/2009 | Nilsson et al. |
| 2010/0130607 A1 | 5/2010 | Gold |
| 2010/0144651 A1 | 6/2010 | Nilsson et al. |
| 2010/0324327 A1 | 12/2010 | Lee |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0020954 A1 | 1/2012 | Achiron et al. |
| 2012/0034274 A1 | 2/2012 | Nilsson et al. |
| 2012/0034303 A1 | 2/2012 | Nilsson et al. |
| 2012/0165404 A1 | 6/2012 | Lukashev |
| 2012/0196931 A1 | 8/2012 | Lukashev et al. |
| 2012/0196940 A1 | 8/2012 | Brown et al. |

FOREIGN PATENT DOCUMENTS

| | | |
|---|---|---|
| CN | 1600100 A | 3/2005 |
| CN | 101056624 A | 10/2007 |
| CN | 101056624 A | 10/2007 |
| CN | 101318901 A | 12/2008 |
| CN | 101475477 A | 7/2009 |
| CN | 101701943 A | 5/2010 |
| DE | 25 30 372 | 1/1977 |
| DE | 2621214 A1 | 11/1977 |
| DE | 27 03 964 | 8/1978 |
| DE | 28 40 498 | 8/1979 |
| DE | 38 34 794 A1 | 4/1990 |
| DE | 3834794 A1 | 4/1990 |
| EP | 0 312 697 | 4/1989 |
| EP | 0 349 235 | 1/1990 |
| EP | 0 518 388 | 12/1992 |
| EP | 1123092 B1 | 8/2002 |
| EP | 2316430 A1 | 5/2011 |
| GB | 1 153 927 | 6/1969 |
| GB | 1153927 A | 6/1969 |
| JP | 2004-518676 A | 6/2004 |
| RU | 2138254 C1 | 9/1999 |
| RU | 2138254 C9 | 9/1999 |
| WO | WO 89/01930 | 3/1989 |
| WO | WO 96/19184 | 6/1996 |
| WO | WO 96/32942 | 10/1996 |
| WO | WO 97/48371 | 12/1997 |
| WO | WO 98/04290 | 2/1998 |
| WO | WO 98/35666 | 8/1998 |
| WO | WO 98/52549 | 11/1998 |
| WO | WO 99/49858 | 10/1999 |
| WO | WO 00/12072 | 3/2000 |
| WO | WO 00/23068 | 4/2000 |
| WO | WO-00/23068 A2 | 4/2000 |
| WO | WO 00/30622 | 6/2000 |
| WO | WO 01/51047 | 7/2001 |
| WO | WO 01/96281 | 12/2001 |
| WO | WO 02/055063 | 7/2002 |
| WO | WO 02/055066 | 7/2002 |
| WO | WO 02/055067 | 7/2002 |
| WO | WO-02058677 A1 | 8/2002 |
| WO | WO 03/004001 | 1/2003 |
| WO | WO-03/004001 A1 | 1/2003 |
| WO | WO 03/028742 | 4/2003 |
| WO | WO 03/041705 | 5/2003 |
| WO | WO-03/08003 A2 | 10/2003 |
| WO | WO 03/080034 | 10/2003 |
| WO | WO 2004/018452 | 3/2004 |
| WO | WO-2007/012031 A1 | 3/2004 |
| WO | WO 2004/084920 | 10/2004 |
| WO | WO 2004/098617 | 11/2004 |
| WO | WO 2004/098618 | 11/2004 |
| WO | WO 2004/098619 | 11/2004 |
| WO | WO 2004096185 A1 | 11/2004 |
| WO | WO 2004/103370 | 12/2004 |
| WO | WO-2005/016318 A1 | 2/2005 |
| WO | WO-2005089726 A1 | 9/2005 |
| WO | WO 2005/105099 | 11/2005 |
| WO | WO-2006/037342 A2 | 4/2006 |
| WO | WO 2006037342 A2 | 4/2006 |
| WO | WO 2006/050730 | 5/2006 |
| WO | WO 2007/006307 | 1/2007 |
| WO | WO 2007/006308 | 1/2007 |
| WO | WO-2007/0063070 A2 | 1/2007 |
| WO | WO 2007/042034 | 4/2007 |
| WO | WO 2007/042035 | 4/2007 |
| WO | WO-2007133583 A2 | 11/2007 |
| WO | WO 2007/148744 | 12/2007 |
| WO | WO 2008/096271 | 8/2008 |
| WO | WO 2010/079222 | 7/2010 |
| WO | WO 2010079221 A1 | 7/2010 |
| WO | WO 2011/100589 | 8/2011 |

OTHER PUBLICATIONS

Anon., "Handbook of Pharmaceutical Excipients" entry for Polyethyleneglycol, translated into Japanese by the Pharmaceutical Society of Japan, pp. 334-340 (1989).

Anon., "Handbook of Pharmaceutical Excipients" entry for Hydroxypropyl cellulose, translated into Japanese by the Pharmaceutical Society of Japan, pp. 281-285 (1989).

Anon., "Handbook of Pharmaceutical Excipients" entry for Methacrylic acid copolymer, polymericmethacrylates, translated by the Pharmaceutical Society of Japan, pp. 359-361 (1989).

Arnold et al., "[IN3-2.002] Effect of BG-12 on brain atrophy and lesions volume: MRI results from the DEFINE study during first and second year of treatment," *Neurology* 78:IN3-2.002 (2012).

Arnold et al., "[P02.121] Neuroprotective effects of BG-12 on malonate-induced striatal lesion volume in Sprague-Dawley rat brain," *Neurology* 78:P02.121 (2012).

Arnold et al., "[S11.003] Effect of BG-12 on brain atrophy and lesions volume: MRI results from the DEFINE study during first and second year of treatment," *Neurology* 78:S11.003 (2012).

Arnold et al., "[S11.004] Effects of BG-12 on magnetization transfer ratio in whole brain and normal-appearing brain tissue: Findings from the DEFINE study," *Neurology* 78:S11.004 (2012).

Arnold et al., "Efficacy on MRI endpoints of BG-12, an oral therapy, in relapsing-remitting multiple sclerosis: data from the phase 3 DEFINE trial," *Mult. Scler. J.* 17:S369 (Abstract P831) (2011).

Asadullah et al., "Influence of monomethylfumarate on monocytic cytokine formation—explanation for adverse and therapeutic effects in psoriasis?," *Arch. Dermatol. Res.* 289:623-630 (1997).

Bar-Or et al., "[P01.130] Effect of BG-12 in subgroups of patients with relapsing-remitting multiple sclerosis: Findings from the DEFINE study," *Neurology* 78:P01.130 (2012).

Beebe et al., "[P05.034] The active metabolite of BG-12, monomethyl fumarate ils transported across the blood-brain barrier:

(56) References Cited

OTHER PUBLICATIONS single- and multiple-dose studies in mice," Annual Meeting of the American Academy of Neurology 2011 Session P05: Multiple Sclerosis: Models (Apr. 13, 2011).
Bista et al., "[P02.108] Dimethyl fumarate suppresses inflammation in vitro via both Nrf2-dependent and Nrf2-independent pathways," *Neurology* 78:P02.108 (2012).
Feinstein et al., "BG-12 exhibits anti-inflammatory and prometabolic effects in brain astrocytes," *Mult. Scler. J.* 16:S309 (Abstract P879) (2010).
Fox et al., "(S34) Phase 3 clinical program to assess efficacy and safety of BG00012 in MS," *Int. J. MS Care* 9:59 (Abstract S34) (2007).
Fox et al., "[S01.003] Clinical efficacy of BG-12 in relapsing-remitting multiple sclerosis (RRMS): Data from the phase 3 CONFIRM study," *Neurology* 78:S01.003 (2012).
Fox et al., "Placebo-controlled phase 3 study of oral BG-12 or glatiramer in multiple sclerosis," *N. Engl. J. Med.* 367:1087-1097 (2012).
Friedrich et al., "Addition of pentoxifylline could reduce the side effects of fumaric acid esters in the treatment of psoriasis," *Acta Derm. Venereol.* 81:429-430 (2001).
Giovannoni et al., "[PD5.005] BG-12 increases the proportion of patients free of clinical and radiologic disease activity in relapsing-remitting multiple sclerosis: Findings from the DEFINE study," *Neurology* 78:PD5.005 (2012).
Gold et al., "Clinical efficacy of BG-12, an oral therapy, in relapsing-remitting multiple sclerosis: Data from the phase 3 DEFINE trial," *Mult. Scler. J.* 17:S34 (Abstract 95) (2011).
Gold et al., "Safety of a novel oral single-agent fumarate, BG00012, in patients with relapsing-remitting multiple sclerosis: results of a phase 2 study," *J. Neurol.* 253 [Suppl 2]: II/144-145 (Abstract P573) (2006).
Gold et al., "Two phase 3 studies to determine the efficacy and safety of BG00012, a novel, oral fumaric acid derivative, in patients with relapsing multiple sclerosis," *Mult. Scler.* 13:S173 (Abstract P579) (2007).
Gold et al., "Placebo-controlled phase 3 study of oral BG-12 for relapsing multiple sclerosis," *N. Engl. J. Med.* 367:1098-1107 (2012).
Jin et al., "Novel dosage form of controlled release of drug," Chemical Industry Press, p. 109 (2005) (English Language Translation Provided) (4 pages).
Kappos et al., "BG-12 effects on patient-reported outcomes in relapsing-remitting multiple sclerosis: Results from the DEFINE study," *Mult. Scler. J.* 17:S488 (Abstract P1071) (2011).
Kappos et al., "Efficacy and safety of oral fumarate in patients with relapsing-remitting multiple sclerosis: a multicentre, randomised, double-blind, placebo-controlled phase IIB study," *Lancet* 372:1463-1472 (2008).
Kappos et al., "Efficacy of a novel oral single-agent fumarate, BG00012, in patients with relapsing-remitting multiple sclerosis: results of a phase 2 study," *J. Neurol.* 253 [Suppl 2]:II/27 (Abstract O108) (2006).
Kolbach et al., "Fumaric acid therapy in psoriasis: Results and side effects of 2 years of treatment," *J. Am. Acad. Dermatol.* 27:769-771 (1992).
Kreuter et al., "Treatment of disseminated granuloma annulare with fumaric acid esters," *BMC Dermatol.* 2:5 (2002) (4 pages).
Kreuter et al., "Fumaric acid esters in necrobiosis lipoidica: Results of a prospective noncontrolled study," *Br. J. Dermatol.* 153:802-807 (2005).
Lee et al., "Spotlight on fumarates," *Int. MS J.* 15:12-18 (2008).
Lehmann et al., "Fumaric acid esters are potent immunosuppressants: Inhibition of acute and chronic rejection in rat kidney transplantation models by methyl hydrogen fumarate," *Arch. Dermatol. Res.* 294:399-404 (2002).
Linker et al., "[P07.196] Superior effects of combination therapy with BG-12 (dimethylfumarate) and interferon beta in experimental autoimmune encephalomyelitis," Annual Meeting of the American Academy of Neurology 2011 Session P07: Multiple Sclerosis: Interventions IV (Apr. 14, 2011).
Litjens et al., "Monomethylfumarate affects polarization of monocyte-derived dendritic cells resulting in down-regulated Th1 lymphocyte responses," *Eur. J. Immunol.* 34:565-575 (2004).
Litjens et al., "Pharmacokinetics of oral fumarates in healthy subjects," *Br. J. Clin. Pharmacol.* 58:429-432 (2004).
MacManus et al., "BG-12 reduces evolution of new enhancing lesions to T1-hypointense lesions in patients with multiple sclerosis," *J. Neurol.* 258:449-456 (2011).
Methner et al., "[P01.200] Dimethylfumarate protects hippocampal cells from oxidative stress by increasing glutathione," Annual Meeting of the American Academy of Neurology 2011 Session P01: Multiple Sclerosis: Medication Safety: Long Term Follow-Up (Apr. 11, 2011).
Miller et al., "[S11.001] Effects of BG-12 on magnetic resonance imaging (MRI) endpoints in patients with relapsing-remitting multiple sclerosis (RRMS): Data from the phase 3 CONFIRM study," *Neurology* 78:S11.001 (2012).
Mrowietz et al., "Treatment of severe psoriasis with fumaric acid esters: Scientific background and guidelines for therapeutic use. The German Fumaric Acid Ester Consensus Conference," *Br. J. Dermatol.* 141:424-429 (1999).
Phillips et al., "[S41.005] Safety and tolerability of BG-12 in patients with relapsing-remitting multiple sclerosis (RRMS): analyses from the CONFIRM study," *Neurology* 78:S41.005 (2012).
Reddingius, "Bioanalysis and pharmacokinetics of fumarates in humans," Dissertation ETH Zurich No. 12199 (1997) (160 pages).
Scannevin et al., "[P05.037] Neuroprotective effects of BG-12 and other fumarates on primary cultures of neurons and astrocytes after oxidative challenge," Annual Meeting of the American Academy of Neurology 2011 Session P05: Multiple Sclerosis: Models (Apr. 13, 2011).
Scannevin et al., "Neuroprotective effects of dimethyl fumarate and monomethyl fumarate on primary cultures of human spinal cord astrocytes after oxidative challenge," *Mult. Scler. J.* 16:S312 (2010) (Abstract P887).
Schilling et al., "Fumaric acid esters are effective in chronic experimental autoimmune encephalomyelitis and suppress macrophage infiltration," *Clin. Exp. Immunol.* 145:101-107 (2006).
Schimrigk et al., "Oral fumaric acid esters for the treatment of active multiple sclerosis: an open-label, baseline-controlled pilot study," *Eur. J. Neurol.* 13:604-610 (2006).
Sebök et al., "Effect of fumaric acid, its dimethylester, and topical antipsoriatic drugs on epidermal differentiation in the mouse tail model," *Skin Pharmacol.* 9:99-103 (1996).
Selmaj et al., "Safety and tolerability of BG-12 in the phase 3 DEFINE trial in patients with relapsing-remitting multiple sclerosis," *Mult. Scler. J.* 17:S451 (2011) (Abstract P994).
Sheikh et al., "[P04.136] Safety, tolerability, and pharmacokinetics of BG-12 administered with and without aspirin: key findings from a randomized, double-blind, placebo-controlled trial in healthy volunteers," *Neurology* 78:P04.136 (2012).
van Horssen et al., "[P02.183] BG-12 (Dimethyl Fumarate): A novel therapeutic to promote oligodendrocyte survival?," Annual Meeting of the American Academy of Neurology 2011, Session P02: Multiple Sclerosis: Immunology I (Apr. 12, 2011).
Werdenberg et al., "Presystemic metabolism and intestinal absorption of antipsoriatic fumaric acid esters," *Biopharm. Drug Dispos.* 24:259-273 (2003).
Woodworth et al., "Oral BG-12 in combination with interferon beta-1 a or glatiramer acetate: pharmacokinetics, safety and tolerability," *Mult. Scler. J.* 16:S160 (2010) (Abstract P478).
Psoriasis—the overview [online], retrieved on Sep. 27, 2010 from www.webmd.com/skin-problems-and-treatments/psoriasis/understanding-psoriasis-basics.
Psoriasis—prevention [online], retrieved on Sep. 27, 2010 from www.webmd.com/skin-problems-and-treatments/psoriasis/psoriasis-prevention.
Multiple sclerosis [online], retrieved on Sep. 27, 2010 from www.nlm.nih.gov/medlineplus/ency/article/0007373.htm

(56) References Cited

OTHER PUBLICATIONS

International Search Report for International Application No. PCT/DK2006/000402, completed Dec. 13, 2006, mailed Dec. 20, 2006 (4 pages).
International Preliminary Report on Patentability for International Application No. PCT/DK2006/000402, issued Jan. 9, 2008 (7 pages).
Written Opinion of the International Searching Authority for International Application No. PCT/DK2006/000402, completed Dec. 13, 2006 (6 pages).
International Search Report for International Application No. PCT/DK2006/000403, completed Aug. 28, 2006, mailed Sep. 25, 2006 (3 pages).
International Preliminary Report on Patentability for International Application No. PCT/DK2006/000403, issued Jan. 9, 2008 (8 pages).
Written Opinion of the International Searching Authority for International Application No. PCT/DK2006/000403, completed Aug. 28, 2006, (7 pages).
International Search Report for International Application No. PCT/DK2005/000648, completed May 17, 2006, mailed May 23, 2006 (6 pages).
International Preliminary Report on Patentability for International Application No. PCT/DK2005/000648, dated May 4, 2007 (10 pages).
Written Opinion of the International Searching Authority for International Application No. PCT/DK2005/000648, completed May 17, 2006 (7 pages).
PCT Demand for International Application No. PCT/DK2005/000648, dated Aug. 23, 2006, receipt date of Aug. 25, 2006 (16 pages).
International Search Report for International Application No. PCT/DK2006/000561, completed Feb. 1, 2007, mailed Feb. 14, 2007 (5 pages).
International Preliminary Report on Patentability for International Application No. PCT/DK2006/000561, dated Apr. 8, 2007 (10 pages).
Written Opinion for International Application No. PCT/DK2006/000561, completed Feb. 1, 2007 (9 pages).
International Search Report for International Application No. PCT/DK2006/000563, completed Mar. 23, 2007, mailed Apr. 4, 2007 (10 pages).
International Preliminary Report on Patentability for International Application No. PCT/DK2006/000563, issued Apr. 8, 2008 (11 pages).
Written Opinion of the International Searching Authority for International Application No. PCT/DK2006/000563, completed Mar. 23, 2007 (10 pages).
International Search Report for International Application No. PCT/EP2010/050172, completed Mar. 25, 2010, mailed Apr. 13, 2010 (2 pages).
International Preliminary Report on Patentability for International Application No. PCT/EP2010/050171, dated Jul. 12, 2011 (5 pages).
International Preliminary Report on Patentability for International Application No. PCT/EP2010/050172 with annexes, dated Apr. 5, 2011 (33 pages).
Written Opinion of the International Searching Authority for International Application No. PCT/EP2010/050172, completed Mar. 25, 2010, mailed Apr. 13, 2010 (6 pages).
PCT Demand for International Application No. PCT/EP2010/050172, dated Nov. 9, 2010 (35 pages).
Communication Pursuant to Article 94(3) EPC for European Patent Application No. 05789026.1, dated Sep. 11, 2008 (3 pages).
Reply to Communication Pursuant to Article 94(3) EPC for EP patent application No. 05789026.1, dated Mar. 23, 2009 (20 pages).
Reply to Communication Pursuant to Rule 112(1) EPC for EP Application No. 05789026.1, dated Mar. 5, 2010 (21 pages).
Communication Pursuant to Article 96(2) EPC for European Patent Application No. 05800741.0, dated Aug. 30, 2007 (4 pages).
Reply to Communication Pursuant to Article 96(2) EPC for European Patent Application No. 05800741.0, dated Mar. 10, 2008 (8 pages).

Communication Pursuant to Article 94(3) EPC for EP Patent Application No. 06753339.8, dated Jul. 14, 2008 (2 pages).
Reply to Communication Pursuant to Article 94(3) EPC for EP Patent Application No. 06753339.8, dated Jan. 23, 2009 (16 pages).
Communication Pursuant to Article 94(3) EPC for EP Patent Application No. 06753339.8, dated Aug. 9, 2010 (3 pages).
Communication Pursuant to Article 94(3) EPC for European Patent Application No. 06753340.6, dated Jun. 13, 2008 (4 pages).
Reply to Communication Pursuant to Article 94(3) EPC for European Patent Application No. 06753340.6 dated Dec. 15, 2008 (19 pages).
Communication Pursuant to Article 94(3) EPC for European Patent Application No. 06753340.6, dated Jan. 9, 2009 (3 pages).
Reply to Communication Pursuant to Article 94(3) EPC for European Patent Application No. 06753340.6, dated May 4, 2009 (4 pages).
Communication Pursuant to Article 94(3) EPC for European Patent Application No. 06791453.1, dated Nov. 13, 2008 (11 pages).
Reply to Communication Pursuant to Article 94(3) EPC for European Patent Application No. 06791453.1, dated Apr. 17, 2009 (18 pages).
Communication Pursuant to Rule 62 EPC for European Patent Application No. 10182198.1, dated Mar. 28, 2011 (7 pages).
Reply to Communication Pursuant to Rules 161/162 EPC for European Patent Application No. 10700730.4, dated Jan. 20, 2012 (51 pages).
Communication Pursuant to Article 94(3) EPC for European Patent Application No. 10700730.4, dated May 30, 2012 (3 pages).
First Office Action issued in Chinese Patent Application No. 200580038572.8, date of notification Feb. 6, 2009 (English Language Translation Provided) (12 pages).
Second Office Action issued in Chinese Patent Application No. 200580038572.8, date of notification Nov. 27, 2009 (English Language Translation Provided) (11 pages).
Third Office Action issued in Chinese Patent Application No. 200580038572.8, date of notification Aug. 25, 2010 (English Language Translation Provided) (13 pages).
Fourth Office Action issued in Chinese Patent Application No. 200580038572.8, date of notification Feb. 11, 2011 (English Language Translation Only) (5 pages).
First Examination Report issued in Indian Patent Application No. 1583/KOLNP/2007, dated Jan. 3, 2011 (3 pages).
First Office Action issued in Japanese Patent Application No. 2007-535023, issued Oct. 4, 2011 (English Language Translation Provided) (7 pages).
Final Office Action issued in Japanese Patent Application No. 2007-535023, issued Aug. 7, 2012 (English Language Translation Provided) (7 pages).
First Office Action Issued in Chinese Patent Application No. 200680041526.8, date of notification Jan. 15, 2010 (English Language Translation Provided) (17 pages).
Extended European Search Report issued in European Patent Application No. 12193798.1, dated Mar. 20, 2013 (6 pages).
International Search Report and Written Opinion issued in PCT/EP2010/050172 on Mar. 25, 2010.
Official Action (Inquiry) of the State Examination for Russian Patent Application No. 2011128785/15, dated Jun. 5, 2013 (4 pages).
Chapter 14 Tablets. *Industrial Technology of Medicines*. Chueshov B.I., Kharkov, vol. 2, pp. 310-382 (2002) (Russian Language).
Partial English Language Translation of Chapter 14 Tablets. *Industrial Technology of Medicines*. Chueshov B.I., Kharkov, vol. 2, pp. 310-382 (2002).
Notice of Opposition to a European Patent No. 2 316 430, filed by Acino Pharma AG dated Mar. 5, 2013 (21 pages).
Communication pursuant to rule 114(2) EPC enclosing third party observations filed in EP1799196, dated Apr. 16, 2013 (418 pages).
Conclusion on Patentability of the Invention issued in Eurasian Patent Application No. 201290596/28, dated Sep. 12, 2013 (2 pages).
Notice of Opposition to a European Patent No. 2 316 430, filed by Synthon B.V., dated Mar. 6, 2013 (35 pages).
Exhibit A of Submission Applicant: *Preparation of Erosion Matrix Tablets* dated Mar. 5, 2010 for EP1799196 (1 page).
Declaration of Dominique van de Kamp, dated Mar. 5, 2013 (4 pages).
Lieberman et al., *Pharmaceutical Dosage Forms: Tablets* vol. 3, Second Edition, pp. 199, 200, 275, 276 (1990).

(56) References Cited

OTHER PUBLICATIONS

Ansel, *Introduction to Pharmaceutical Dosage Forms* 4th Edition, pp. 167, 170-174 (1985) (No English Translation).
Van Loenen et al., "Fumaarzuurtherapie: van ficte tot werkelijkheid," *Pharmaceutisch Weekblad* 124:894-900 (1989).
Nieboer et al., "Systemic Therapy with Fumaric Acid Derivates: New Possibilities in the Treatment of Psoriasis," *J. Am. Acad. Dermatol.* 20:601-608 (1989).
Nieboer et al., "Fumaric Acid Therapy in Psoriasis: A Double-Blind Comparison Between Fumaric Acid Compound Therapy and Monotherapy with Dimethylfumaric Acid Ester," *Dermatologica* 181:33-37 (1990).
Notice of Opposition to a European Patent No. 2 316 430, filed by Zentiva k.s., dated Mar. 5, 2013 (13 pages).
"Rote Liste" 2000, p. 32/315, "Fumaderm" (No English Language Translation).
Mrowietz et al., "Treatment of Psoriasis with Fumaric Acid Esters: Results of a Prospective Multicentre Study," *Br. J. Derm.* 138:456-460 (1998).
Partial English Language Translation of Chapter 14 Tablets. *Industrial Technology of Medicines.* Chueshov B.I., 310-382 (2002).
Chapter 14 Tablets. *Industrial Technology of Medicines.* Chueshov B.I., 310-382 (2002). (Russian Language).
Notification on the Results of Patentability Examination for Russian Patent Application No. 2011128785/15, dated Nov. 15, 2013 (English language translation provided).
Notice of Opposition to a European Patent No. 2 316 430, filed by Biogen Idec, dated Mar. 6, 2013 (44 pages).
*Hagers Handbuch der pharmazeutischen Praxis.* 2 Methoden. p. 955 (1991) (No English Language Translation).
SmPC of Fumaderm® initial/Fumaderm®, published Jan. 2004 (9 pages) (No English Language Translation Provided).
Nieboer et al., "Systemic Therapy with Fumaric Acid Derivatives: New Possibilities in the Treatment of Psoriasis," *J. Am. Acad. Dermatol.* 20:601-608 (1989).
Bacharach-Buhles et al., "Fumaric Acid Esters (FAEs) Suppress Cd 15- and ODP 4-Positive Cells in Psoriasis," *Acta. Derm. Venerol. (Stockh)* Suppl. 186:79-82 (1994).
Bauer et al., "5.4 Biopharmazeutische Probleme and Grenzen der Wirksamkeit von Uberzugen auf Arzneiformen," pp. 136-139 in *überzogene Arzneiformen.* (1998) (No English Language Traslation Provided).
Voigt, Excerpt from "Lehrbuch der pharmazeutischen Technologie," pp. 209-212, published 1987.
Malka et al., "Controlled Delivery of Fumaric Acid—A New Possibility in the Treatment of Psoriasis," *Proceed. Intl. Symp. Control. Rel. Bioact. Mater.* 25:836-837, 1998.
Kunst, "Fumaarzuurtherapie bij psoriasis," *TIG* pp. 243-251 (1998) (English Language Translation Provided).
Durlinger (editor) et al., "Fumaarzuur" *Psoriant,* 1/04, vol. 22, pp. 1-36 (2004) (English Language Translation Provided).
De Apotheek, Website excerpt from http://mierlohout.nl, 2003 (6 pages).
Declaration of Jacobus C. Rasser, Ph.D. and Annexes 1-7, dated Mar. 4, 2013 (14 pages).
Declaration of Constance Yeung, Ph.D. and Annexes 1-6, dated Mar. 4, 2013 (13 pages).
Declaration of David Goldman, Ph.D., dated Feb. 27, 2013 (2 pages).
Declaration of Oliver Schinzinger, Ph.D., dated Mar. 4, 2013 (2 pages).
Declaration of Pierre Boulas, Ph.D., Michael Szulc, Ph.D., and Yig-ing Lin, Ph.D., and Annexes 1-4 dated Mar. 6, 2013 (43 pages).
Notice of Opposition to a European Patent No. 2 316 430, filed by Medac Gesellschaft für klinische Spezialpräparate mBh, dated Mar. 6, 2013 (30 pages) (English Language Translation Provided).
Langguth et al., "Biopharmazie," Weinheim, pp. 271-272, 2004 (No English Language Translation Provided).
Notice of Opposition to a European Patent No. 2 316 430, filed by Apotheek Mierlo-Hout, dated Mar. 6, 2013 (44 pages).
Kreuter et al., "Treatment of Disseminated Granuloma Annulare with Fumaric Acid Esters," *BMC Dermatology* 2:5 (2002) (3 pages).
Mrowietz et al., "Treatment of Severe Psoriasis with Fumaric Acid Esters: Scientific Background and Guidelines for Therapeutic Use," *Br. J. Dermatol.* 141:424-429 (1999).
Litjens et al., "Pharmacokinetics of Oral Fumarates in Healthy Subjects," *Br. J. Clin. Pharm.* 58:429-432 (2004).
Najarian and Gottlieb, "Connections between Psoriasis and Crohn's Disease," *J. Am. Acad. Dermatol.* 48:805-824 (2003).
Altmeyer et al., "Antipsoriatic Effect of Fumaric Acid Derivatives," *J. Am. Acad. Dermatol.* 30:977-981 (1994).
Ojetti et al., "High Prevalence of Celiac Disease in Psoriasis," *Am. J. Gastroenterol.* 98:2574-2575 (2003).
"Aqueous EUDRAGI® Coatings Enable GI Targeting with Capsules," *Pharma Polymers News* No. 8, pp. 1-2, Oct. 2001.
"It Is Not Only the Polymer that Determines the Properties of the Dosage Form," *Pharma Polymers News* No. 8, pp. 3-4, Oct. 2001.
"Eudragit® Makes it Possible," *Pharma Polymers News* No. 7, p. 1, Oct. 2000.
"New Colon Delivery System Developed," *Pharma Polymers News* No. 7, pp. 2-3, Oct. 2000.
"New Formulation with EUDRAGI® FS 30 D Conveys the Active to the Colon," *Pharma Polymers News* No. 7, p. 4, Oct. 2000.
"Product Line Pharma Polymers Opens Technical Service Centers in Singapore, Shanghai and Mumbai," *Pharma Polymers News* No. 7, p. 5, Oct. 2000.
"EUDRAGI® RL/RS 30 D Provides for Osmotically Controlled Drug Release at Reduced Risk," *Pharma Polymers News* No. 7, p. 6, Oct. 2000.
Balasubramaniam et al., "Fumaric Acid Esters in Severe Psoriasis, Including Experience of Use in Combination with Other Systemic Modalities," *Br. J. Dermatol.* 150:741-746 (2004).
Kunst, "Fumaarzuurtherapie bij psoriasis," *TIG* pp. 243-251 (1998) (English Language Translation).
Analyserapport, "dimethylfumaraat, tabletten," RegiLabs BV, dated Sep. 24, 2009 (No English Language Translation) (26 pages).
*Psoriant*, 1/04, vol. 22, pp. 1-36 (2004) (English Language Translation).
Notice of Opposition to a European Patent No. 2 316 430, filed by Dr. Christian Hollatz dated Mar. 6, 2013 (18 pages).
List of medicaments on offer from Mierlo Hoult Phramacy, Netherlands, including Psoinovo® 30 mg and 120 mg, dated Jan. 1, 2004.
In vitro dissolution test of Psorinovo tablet dated Mar. 6, 2013.
"Rote Liste" 1997, p. 32/330, "Fumaderm".
Excerpt from Bauer and Fromming, "Lehrbuch der pharmazeutischen Technologie," Wissenschaftliche Verlagsgesellschaft Stuggart, p. 371, 2002.
De Haan et al., "Oral Controlled Release Dosage Forms. A Review," *Pharmaceutisch Weekblad Scientific Edition* 6:57-67, 1984.
Malka et al., "Controlled Delivery of Fumaric Acid—A New Possibility in the Treatment of Psoriasis," *Proceed. Intl. Symp. Control. Bioact. Mater.* 25:836-837, 1998.
English language translation of the Notice of Opposition as filed at the European Patent Office by the law firm Simandi Meinken on behalf of Wohldorff GmbH dated Dec. 13, 2013.
Notice of Opposition to a European Patent filed by Wohldorff GmbH in European Patent No. EP2379063, filed Dec. 13, 2013.
Ritschel et al., "Die Tablette: Handbuch der Entwicklung; Herstellung and Qualitatssicherung," 2, Auflage, 2002, pp. 136-138.
Official Action for Japanese Patent Application No. 2011-544786 issued Feb. 18, 2014 (8 pages).
English language translation of an Official Action for Japanese Patent Application No. 2012-267572, mailed Feb. 12, 2014.
Nakano M., JJSHP, 31:13-16 (1995).
Pharmaceutical Excipients Dictionary (Yakuji Nippo, Ltd.) pp., 106-107, 1994.
Sogo Seizaigaku (General Galencial Pharmacy) (Nanzando Co., Ltd), pp. 458-459, 2000.
Pharmaceutical Excipients Reference, (Yakuji Nippo, Ltd.), pp. 11-21, 1999.
Notice of Opposition to a European Patent filed by Biogen Idec in European Patent No. EP2379063, filed Dec. 13, 2013.

(56) References Cited

OTHER PUBLICATIONS

Voigt et al., "Pharmazeutische Technologie," 10th Edition, pp. 342-343 (2006).
"Fiedler Encyclopedia of Excipients for Pharmaceutical, Cosmetics, and Related Areas," 6th Edition, vol. 9, 2007 (6 pages).
Upadrashta et al., "Direct compression controlled release tablets using ethylcellulose matrices," Drug Development and Industrial Pharmacy 19:449-460 (1993).
Tabandeh et al., "Preparation of sustained-release matrix tablets of aspirin with ethylcellulose, Eudragit RS100 and Eudragit S100 and studying the release profiles and their sensitivity to tablet hardness," Iranian Journal of Pharmaceutical Research 2:201-206 (2003).
"Handbook of Pharmaceutical Excipients," 4th Edition, p. 289 (2003).
Priority Document of DK PA 2009 00034, filed Jan. 9, 2009.
Priority Document of U.S. Appl. No. 61/143,613, filed Jan. 9, 2009.
Notice of Opposition to a European Patent filed by Generics [UK] Ltd (trading as Mylan) in European Patent No. EP2379063, filed Dec. 13, 2013.
Aulton, "Chapter 28: Coating of tablets and multiparticulates," in "Pharmaceutics: The Science of Dosage Form Design," Elsevier, 2nd Edition, 2002.
Decision on Rejection for Chinese Patent Application No. 201080011800.3, issued Feb. 27, 2014 (10 pages).
Conclusion on the patentability of the invention for Eurasian Patent Application No. 201290596/28, mailed Apr. 25, 2014 (2 pages).
Record of Examiners Meeting for Russian Application No. 2011128758/15, dated Sep. 1, 2014 (3 pages).

\* cited by examiner

PHARMACEUTICAL FORMULATION COMPRISING ONE OR MORE FUMARIC ACID ESTERS IN AN EROSION MATRIX

RELATED APPLICATIONS

This application is a national phase application of International Application No. PCT/EP2010/050172, filed Jan. 8, 2010, which claims priority to Danish Patent Application No. PA 2009 00034, filed Jan. 9, 2009 and U.S. Provisional Patent Application No. 61/143,613, filed Jan. 9, 2009. The entire contents of each of the foregoing applications are hereby incorporated by reference.

FIELD OF THE INVENTION

The present invention relates to a pharmaceutical formulation comprising an erosion matrix. More particularly the invention relates to a pharmaceutical formulation comprising an erodible matrix comprising one or more fumaric acid esters as well as one or more rate-controlling agents, wherein erosion of said erosion matrix permits controlled or sustained release of said fumaric acid esters.

BACKGROUND OF THE INVENTION

Psoriasis is a chronic skin disease, with a high percentage of genetic pre-disposition. The disease fluctuates between acute exacerbation and times of complete standstill. Patients suffering from psoriasis may be severely handicapped because of the external characteristics of the disease. This affects all parts of life, such as the professional career as well as the personal and private life.

The therapeutic possibilities available until the therapy according to the invention are limited, in particular for patients with moderate to severe psoriasis, and many of them provide only a temporary and short-term improvement, and/or have severe adverse effects/side effects. Since psoriasis has a high recurrence rate, the majority of patients have to undergo long-term treatment.

Fumaric acid esters have been used for the treatment of moderate to severe psoriasis for more than 30 years. In 1994 a defined mixture of dimethyl fumarate and monoethyl fumarate salts was approved in Germany—Fumaderm® initial/Fumaderm®. One enteric coated tablet of Fumaderm® contains the following active ingredients: dimethylfumarate 120 mg; ethylhydrogenfumarate, calcium salt 87 mg; ethylhydrogenfumarate, magnesium salt 5 mg; ethylhydrogenfumarate, zink salt 3 mg, and the following other ingredients: croscarmellose-sodium, talc, magnesium stearate, coloring agents E 171 and E 132, methacrylic acid-methylmethacrylate-copolymer (1:1), methacrylic acid-ethylacrylate-copolymer (1:1), Macrogol 6000, simethicone, povidone, triethyl citrate, microcrystalline cellulose, highly disperse silicon dioxide [Summary of Product Characteristics, Fumaderm®, version January 2009]. By today Fumaderm® represents about 66% of all prescriptions for systemic therapy of psoriasis in Germany. However, a high frequency of side effects causes some patient discontinuation early in treatment. It is contemplated that the gastrointestinal side effects and flushing can, at least partially, be explained by the release properties of the prescription formulation, leading to high local concentrations in the intestines.

The present inventors contemplate that an improved treatment regimen may be obtained by administration of a pharmaceutical composition that is designed to deliver the active substance in a controlled manner, i.e. in a manner that is prolonged, sustained, retarded, slow and/or delayed compared with the commercially available product.

Fumaric acid esters, such as dimethyl fumarate, can be subject to degradation and hydrolysis. It is e.g. known that dimethyl fumarate is more prone to hydrolysis in an alkaline/less acidic environment, c.f. more acidic environments (Litjens et al, "In vitro pharmacokinetics of anti-psoriatic fumaric acid esters", BMC Pharmacology 2004, 4:22). Thus, dimethyl fumarate is considered to be more prone to hydrolysis in the small intestine, c.f. the gastric ventricle. In addition to the pH effect described above, esterases are considered to contribute to hydrolysis of fumaric acid esters.

WO 2006/037342 discloses controlled release pharmaceutical compositions comprising fumaric acid ester(s) as active substance(s) wherein the controlled release profile results in a reduction in GI (gastro-intestinal) related side-effects.

OBJECT OF THE INVENTION

It is an object of embodiments of the invention to provide a controlled or sustained release pharmaceutical formulation, comprising fumaric acid ester(s) as active substance(s) which shows reduced GI (gastro-intestinal) related side-effects and/or reduced flushing over the prior art Fumaderm® formulation. A further object of the present invention is to provide a controlled or sustained release pharmaceutical formulation comprising fumaric acid ester(s) as active substance(s) which has an improved pharmacokinetic profile over prior art formulations. In particular, it is an object of the present invention to provide a controlled or sustained release pharmaceutical formulation comprising fumaric acid ester(s) as active substance(s) which shows a reduced variability in AUC and/or $C_{max}$ values over prior art controlled release formulations. In particular, it is an object of the present invention to provide a controlled or sustained release pharmaceutical formulation comprising fumaric acid ester(s) as active substance(s) which shows an adequate relative bioavailability c.f. e.g. the prior art Fumaderm® formulation. Specifically, it is an object of the present invention to provide a controlled or sustained release pharmaceutical formulation comprising fumaric acid ester(s) as active substance(s) which shows a reduced variability in AUC and/or Cmax values over the prior art Fumaderm® formulation.

SUMMARY OF THE INVENTION

It has been found by the present inventor(s) that a controlled or sustained release of one or more fumaric acid esters may be obtained by an erosion matrix tablet. The prolongation of the release of API can be controlled with the amount of rate controlling polymer(s) in relation to the other components and it is contemplated that high local concentrations of the API can be avoided or reduced.

It has been found that a controlled or sustained release of one or more fumaric acid esters at a pharmaceutically relevant level may be obtained from a—compared to Fumaderm®—small tablet in order to improve patient compliance, and wherein high local concentrations of the API may be avoided while securing as complete as possible a delivery of the active substance within a defined time period after reaching the site of absorption, and wherein at the same time a reduced variability, compared to Fumaderm® may be provided.

It has been found that formulations according to the invention exhibit a good in vitro/in vivo correlation. In an aspect the in vitro/in vivo correlation is determined by comparing the time to 80% of the fumaric acid ester being released from the formulations in an in vitro dissolution test to the Cmax being measured in vivo after administration of the formulations.

It is further contemplated by the present inventors that the controlled release of the API by erosion of the matrix minimizes or reduces the exposure of API to hydrolysis within the gastrointestinal tract, thereby mitigating degradation of the API prior to absorption.

In a first aspect, it is contemplated that it is hereby possible to retain the treatment effect while at the same time substantially reducing some or several of the undesired side effects or adverse effects known from Fumaderm®, or improving tolerability c.f. Fumaderm®.

In another aspect, it is contemplated that it is hereby possible to obtain an improved treatment effect compared to Fumaderm® while at the same time reducing the undesired side-effects known from said prior art Fumaderm® treatment of psoriasis.

In another aspect, it is contemplated that it is hereby possible to obtain an improved treatment effect while at the same time maintaining tolerability c.f. Fumaderm®.

In a further aspect, it is contemplated that it is hereby possible to obtain an improved treatment effect while at the same time improving tolerability c.f. Fumaderm®.

In a first aspect the present invention relates to a pharmaceutical formulation in the form of an erosion matrix tablet comprising:
  i) 10% to 80% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and
  ii) 1-50% by weight of one or more rate-controlling agents;
wherein erosion of said erosion matrix permits controlled or sustained release of said active substance.

In an aspect, the present invention relates to a pharmaceutical formulation in the form of an erosion matrix tablet comprising:
  i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and
  ii) 3-40% by weight of one or more rate-controlling agents;
wherein erosion of said erosion matrix permits controlled or sustained release of said active substance.

In an aspect the present invention relates to a pharmaceutical formulation in the form of a monolithic erosion matrix tablet comprising:
  i) 10% to 80% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and
  ii) 1-50% by weight of one or more rate-controlling agents;
wherein erosion of said erosion matrix permits controlled or sustained release of said active substance.

In an aspect the present invention relates to a pharmaceutical formulation in the form of a monolithic erosion matrix tablet comprising:
  i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and
  ii) 3-40% by weight of one or more rate-controlling agents;
wherein erosion of said erosion matrix permits controlled or sustained release of said active substance.

In an aspect the present invention relates to a pharmaceutical formulation in the form of an erosion matrix tablet comprising:
  A) A tablet core comprising:
    i) 40-60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance,
    ii) 4-6% by weight of a rate-controlling agent;
    iii) 35-55% by weight of a binder;
  B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to about 5% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of an erosion matrix tablet comprising:
  A) A tablet core comprising:
    i) 30-60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance,
    ii) 3-6% by weight of a rate-controlling agent;
    iii) 35-65% by weight of a binder;
  B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to about 5% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of a monolithic erosion matrix tablet comprising:
  A) A tablet core comprising:
    i) 40-60% by weight of one or more fumaric acid esters selected from di-($C_1$-$C_5$)alkylesters of fumaric acid and mono-$(C_1-C_5)$alkylesters of fumaric acid, or a pharmaceutically acceptable salt thereof, as an active substance,
ii) 4-6% by weight of a rate-controlling agent;
iii) 35-55% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to about 5% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of a monolithic erosion matrix tablet comprising:
A) A tablet core comprising:
i) 30-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 3-6% by weight of a rate-controlling agent;
iii) 35-65% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to about 5% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of an erosion matrix tablet comprising:
A) A tablet core comprising:
i) 30-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 3-6% by weight of a rate-controlling agent;
iii) 35-65% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of a monolithic erosion matrix tablet comprising:
A) A tablet core comprising:
i) 30-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 3-6% by weight of a rate-controlling agent;
iii) 35-65% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

In an aspect the present invention relates to a pharmaceutical formulation in the form of an erosion matrix tablet comprising:
A) A tablet core comprising:
i) 30-60% by weight of dimethyl fumarate,
ii) 3-6% by weight of hydroxypropyl cellulose;
iii) 35-65% by weight of lactose;
B) an enteric coating in an amount of about 1.5-3.5% by weight of the core;
wherein erosion of said erosion matrix results in release of the dimethyl fumarate—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to about 5% w/w of the dimethyl fumarate contained in the formulation is released, and/or
within the first 3 hours after start of the test from about 20% w/w to about 75% w/w of the dimethyl fumarate contained in the formulation is released, and/or within the first 4 hours after start of the test from about 50% w/w to about 98% w/w of the fumaric ester contained in the formulation is released, and/or within the first 5 hours after start of the test from about 70% w/w to about 100% w/w of the total amount of the dimethyl fumarate contained in the formulation is released.

In an aspect the present invention relates to a pharmaceutical formulation in the form of a monolithic erosion matrix tablet comprising:

A) A tablet core comprising:
  i) 30-60% by weight of dimethyl fumarate,
  ii) 3-6% by weight of hydroxypropyl cellulose;
  iii) 35-65% by weight of lactose;
B) an enteric coating in an amount of about 1.5-3.5% by weight of the core;

wherein erosion of said erosion matrix results in release of the dimethyl fumarate—when subjected to an in vitro dissolution test employing 0.1 N hydrochloric acid as dissolution medium during the first 2 hours of the test and then 0.05 M phosphate buffer pH 6.8 as dissolution medium—as follows:

within the first 2 hours after start of the test from about 0% w/w to about 5% w/w of the dimethyl fumarate contained in the formulation is released, and/or within the first 3 hours after start of the test from about 20% w/w to about 75% w/w of the dimethyl fumarate contained in the formulation is released, and/or within the first 4 hours after start of the test from about 50% w/w to about 98% w/w of the fumaric ester contained in the formulation is released, and/or within the first 5 hours after start of the test from about 70% w/w to about 100% w/w of the total amount of the dimethyl fumarate contained in the formulation is released.

In the present context the term "% by weight" refers to the percentage by weight of each ingredient in the core tablet, thus excluding any exterior coatings or films.

In another aspect the present invention relates to a method for preparing the formulation according to the invention, comprising the steps of:

a) Dissolving or suspending either one or both of a fumaric acid ester and a rate-controlling agent in the form of a polymeric matrix material in water to obtain an aqueous suspension thereof;
b) Spraying said aqueous suspension on granules of a fumaric acid ester and/or a binder for a period of time sufficient to obtain a uniform coating thereon;
c) Drying the granules obtained;
d) Optionally sieving or milling said granules;
e) Blending of any pharmaceutically acceptable excipients and additives in a manner known per se to obtain a tablet formulation;
f) Optionally film or enteric coating of said tablet formulation in a manner known per se;

wherein any of or all of the above steps are performed at a temperature to allow a product temperature not exceeding 45° C.

It is known that e.g. dimethyl fumarate may be lost to sublimation, and the sublimation is more pronounced at higher temperatures.

In some aspects the manufacturing of formulations according to the invention is carried out at relatively low temperature, to minimize or reduce sublimation, and involving few intermediate steps and minimal involvement of non-machine operated steps. These factors contribute to the manufacturing process being scalable and feasible in a commercial setting and at a commercial scale. In some aspects it has been found that formulations according to the invention can be manufactured at larger scale, such as at least 15 kg scale, such as at least 20 kg scale, such as at least 30 kg scale.

In another aspect the present invention relates to a method for preparing the formulation according to the invention, comprising the steps of:

a) Dissolving or suspending a rate-controlling agent in the form of a polymeric matrix material in water to obtain an aqueous suspension thereof;
b) Spraying said aqueous suspension on granules of a fumaric acid ester for a period of time sufficient to obtain a uniform coating thereon;
c) Drying the granules obtained;
d) Optionally sieving or milling said granules;
e) Blending of any pharmaceutically acceptable excipients and additives in a manner known per se to obtain a tablet formulation;
f) Optionally film or enteric coating of said tablet formulation in a manner known per se;

wherein any of or all of the above steps are performed at a temperature to allow a product temperature not exceeding 45° C.

In another aspect, the present invention relates to a method for preparing the formulation according to the invention, comprising the steps of:

a) Optionally sieving or milling crystals of fumaric acid ester;
b) Blending of said crystals of fumaric acid ester, a rate-controlling agent in the form of a polymeric matrix material, and any pharmaceutically acceptable excipients and additives by direct compression to obtain a tablet formulation;
c) Optionally film and/or enteric coating of said tablet formulation in a manner known per se;

wherein any of or all of the above steps are performed at a temperature to allow a product temperature not exceeding 45° C.

In another aspect the pharmaceutical formulation according to the invention is for use for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

Another aspect of the invention is the use of a pharmaceutical formulation according to the invention for the preparation of a medicament for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

Another aspect of the invention is a method of treating psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare, which method comprises administering orally to a patient in need thereof an effective dosage of a pharmaceutical formulation according to the invention

LEGENDS TO THE FIGURE

FIG. 1 shows in vitro dissolution profiles at 37° C. using a paddle dissolution apparatus at 100 rpm employing 0.1 N hydrochloric acid as dissolution medium during the first 2 hours of the test and then followed by 0.05 M phosphate buffer pH 6.8 as dissolution medium for the remaining test period of film and enteric coated erosion matrix tablets according to the invention as described in Examples 16, 18, 20, and 22.

Figure 2:
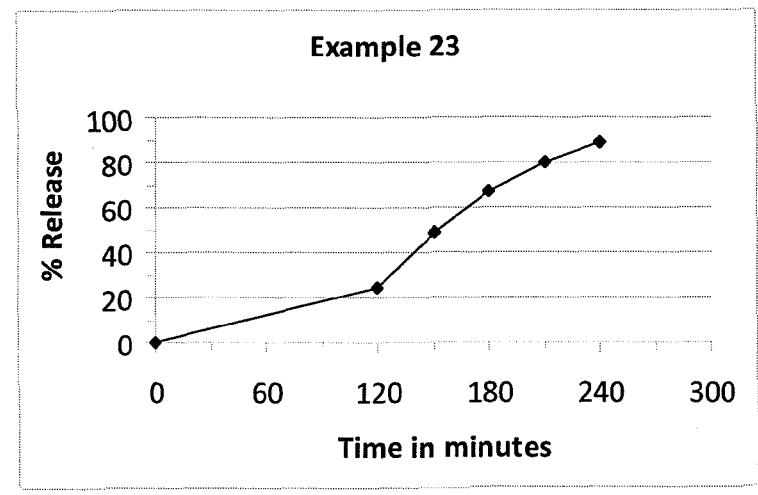

FIG. 2 shows an in vitro dissolution profile at 37° C. using a paddle dissolution apparatus at 100 rpm employing 0.1 N hydrochloric acid as dissolution medium during the first 2 hours of the test and then followed by 0.05 M phosphate buffer pH 6.8 as dissolution medium for the remaining test period of a film coated erosion matrix tablet according to the invention as described in Example 23.

DETAILED DISCLOSURE OF THE INVENTION

In the present context the term "API", which is an abbreviation for "active pharmaceutical ingredient" and the term "active substance" are used interchangeably and refers to the fumaric acid ester(s) that is to be released from the pharmaceutical formulation according to the invention.

In the present context, the term "controlled or sustained release" refer to the release from a formulation that is designed to release the fumaric acid ester in a prolonged, retarded, slow and/or delayed manner compared to the release of the commercially available product Fumaderm®, when tested under comparable conditions (e.g. for in vivo studies: dose equivalents, with or without standardized meal etc., or for in vitro studies: dose equivalents, dissolution test apparatus and working conditions including e.g. composition, volume and temperature of dissolution medium employed, rotation speed etc.).

The release in vivo may be tested by measuring the plasma concentration at predetermined time periods and thereby obtaining a plasma concentration versus time profile for the fumaric acid ester in question or, if relevant, a metabolite thereof. Furthermore, it is contemplated that metabolism already takes place within the gastro-intestinal tract or during passage of the gastro-intestinal mucosa, or upon first passage through the hepatic circulation. Accordingly, when dimethylfumarate is administered, the relevant component to search for in the plasma may be the monomethyl ester and not the dimethylester of fumaric acid.

Other tests may also be used to determine or to give a measure of the release of the active substance in vivo. Thus, animals (e.g. minipigs, dogs etc.) may be used as a model. The animals receive the compositions under investigation and after specified periods of time, blood samples are collected and the content of the active ingredient (or metabolite thereof, if relevant) is determined in plasma or specific organs or extracted from the intestinal contents. Another test involves the use of a specific segment of an animal or human intestine. The segment is placed in a suitable apparatus containing two compartments (a donor and a receiver) separated by the segment, and the composition under investigation is placed in a suitable medium in one compartment (the donor compartment). The composition will release the active substance that subsequently is transported across the intestinal segment. Accordingly, at suitable time intervals, the concentration of the active substance (or, if relevant, the metabolite) is measured in the receiver compartment.

A person skilled in the art will be able to adapt the above-mentioned method to the specific composition.

With respect to in vitro methods, well-established methods are available, especially methods described by official monographs like e.g. United States Pharmacopeia (USP) or the European Pharmacopoeia. A person skilled in the art will know which method to choose and how to select the specific conditions to carry out the in vitro test. For instance, the USP prescribes in vitro tests be carried out at 37+/−1.0 such as 37+/−0.5 degrees Celsius/Centigrade. In one aspect, a suitable dissolution test is one, wherein the dissolution profile is determined as described in the United States Pharmacopoeia at 37° C. using a paddle dissolution apparatus at 100 rpm employing 0.1 N hydrochloric acid as dissolution medium during the first 2 hours of the test and then followed by 0.05 M phosphate buffer pH 6.8 as dissolution medium for the remaining test period. A person skilled in the art will know how to adjust the conditions applied, e.g. temperature, pH, paddle speed, duration etc. In a further aspect, the in vitro dissolution testing is carried out as follows: A USP apparatus II (paddles) with 1 litre vessels is used. Bath temperature is set to 37° C.±0.5° C. and paddle speed to 100 rpm. One tablet is placed in one vessel containing 750 ml 0.1N HCl (pH 1.2) over 2 h. After that the pH is changed to 6.8 by adding 220 ml 0.2 M sodium phosphate buffer. 1.5 ml samples are taken at each sampling time point and analyzed by HPLC for DMF. The HPLC parameters are set as follows: Column: Phenomenex Luna C18, 50×4.6 mm, 3 µm; column oven temperature 30° C., :mobile phase: Methanol:20 mM phosphate buffer pH 3.0 (35:65 V/V), inject volume: 5 µl, Flow rate: 0.8 ml/min, Detector wavelength: 210 nm, run time 5 min, DMF retention time 3.5 min.

In the present context, the term "relative bioavailability" refers to a comparison of the amount of drug absorbed (expressed as area under the curve (AUC)) after administration of two different formulations or reference product. In the present context, the amount of drug absorbed, expressed as AUC, can be detected in the form of the actual drug administered, or as a metabolite thereof. The relative bioavailabilty can be expressed as a percentage of a reference AUC, i.e. AUC In the present context the term "variability" refers to the variability of PK parameters (e.g. Cmax and AUC) after administration of a pharmaceutical formulation or a reference formulation. The variability can be expressed as the coefficient of variation (CV) for a PK parameter, i.e. the ratio of the standard deviation to the mean.

In the present context the term "tolerability" refers to the potential of a drug to be endured by subjects and/or patients. In one aspect, "tolerability" is determined as the potential of a drug to be endured by subjects and/or patients in early stages of treatment, such as within the first three months of start of therapy, such as within the first month of start of therapy, such as within the first two weeks of start of therapy, such as within the first week of start of therapy, such as within the first three days of start of therapy, such as within the first day of start of therapy, such as after the first dose of the therapy. A drug with better tolerability produces fewer side effects in a subject and/or patient c.f. a drug with worse tolerability.

In the present context the term "substantial absence of" refers to a level of less than about 1%, such as less than about 0.5%, such as less than about 0.3%, such as about 0.0%.

In the present context the terms "rate-controlling agent" and "rate-controlling agent in the form of a polymeric matrix material" are used interchangeably and refer to an agent that is able to delay/sustain and/or prolong the in vivo and/or in vitro release of the active substance.

As mentioned above, the in vivo and/or in vitro release of the active substance is prolonged, slow and/or delayed compared with the commercially available Fumaderm® composition. In the present context, the term "prolonged" is intended to indicate that the active substance is released during a longer time period than Fumaderm® such as at least during a time period that is at least 1.2 times, such as, e.g., at least 1.5 times, at least 2 times, at least 3 times, at least 4 times or at least 5 times greater than that of Fumaderm®. Thus, if e.g. 100% of dimethylfumarate is released from Fumaderm® tablets 3 hours after the start of a suitable test, then 100% of dimethylfumarate in a composition according to the invention is released at least 3.6 hours after the start of a suitable test.

In the present context the term "delayed" is intended to indicate that the release of the active substance starts at a later point in time compared with that of Fumaderm® (such as at 30 min or more later such as, e.g., 45 min or more later, 1 hour or more later or 1.5 hours or more later).

In the present context the term "monolithic" refers to consisting of or constituting a single unit.

The formulation according to the invention is contemplated to provide improved tolerability, such as fewer and/or less severe gastrointestinal (GI) side-effects, such as fewer and/or less severe redness episodes, such as fewer and/or less severe flushing episodes.

As used in the present invention, a gastrointestinal (GI) side effect may include, but is not limited to diarrhea, stomach ache, stomach pain, abdominal pain, abdominal cramps, nausea, flatulence, tenesmus, meteorism, an increased frequency of stools, a feeling of fullness and upper abdominal cramps.

In the present context, a reduction of GI related side effects is intended to denote a decrease in severity and/or incidence among a given treated patient population, comparing the GI side effects observed after administration of the formulation according to the invention to the GI side effects observed after administration of Fumaderm®. A reduction in GI related side effects according to this definition could thus be construed as a substantial reduction in incidence of any of the GI side effect listed above, such as at least a 10% reduction in incidence or more preferably at least 20% reduction in incidence or even more preferable a more than 30% reduction in incidence. A reduction in GI related side effect can also be expressed as a substantial reduction in severity in any of the GI side effects listed above, such as a reduction in severity and/or frequency of diarrhea, stomach ache, stomach pain, abdominal pain, abdominal cramps, nausea, flatulence, tenesmus, meteorism, increased frequency of stools, a feeling of fullness or upper abdominal cramps. The reduction of GI related side effects, as described above, can be monitored in a clinical trial setting, either comparing the administration of the formulation according to the invention head on with Fumaderm® or with placebo. In case of a placebo controlled trial, the incidence of GI related side effects in the patients receiving the formulation according to the invention compared to the placebo group, can be compared to historical trials comparing Fumaderm® to placebo (see e.g. Altmeyer et al, J. Am. Acad. Dermatol. 1994; full reference: Altmeyer P J et al, Antipsoriatic effect of fumaric acid derivatives. Results of a multicenter double-blind study in 100 patients. J. Am. Acad. Dermatol. 1994; 30:977-81).

In a further aspect, the formulation according to the invention—upon oral administration and in comparison to that obtained after oral administration of Fumaderm® tablets in an equivalent dosage—reduce (GI) side-effects (frequency and/or severity).

In one embodiment, such a clinical trial can be carried out as described below under "Clinical trial in patients". In another embodiment, such a clinical trial can be carried out as described below under "Clinical trial in healthy volunteers".

Clinical Trial in Patients:

Typically, patients suffering from psoriasis are included in such a study, and typically more than 10% of the body surface area will be affected by psoriasis (severe psoriasis). However, patients in whom between 2 and 10 percent of the body surface area is affected can also be included (moderate psoriasis). Patients can also be selected based on the psoriasis area severity index (PASI) score. Typically, patients within a certain range of PASI scores are included, such as between 10 and 40, or such as between 12 and 30, or such as between 15 and 25. In another embodiment, patients with a certain minimum PASI score are included, such as a PASI score of at least 8, such as at least 10, such as at least 12, such as at least 15. Patients with any type of psoriasis may be included (chronic plaque type, exanthematic guttate type, pustular type, psoriatic erythroderma or palmoplantar type), but in some cases only patients with the chronic plaque type are included. About 15 to 20 patients in each treatment group (formulation according to the invention, Fumaderm® or placebo) are sufficient in most cases, but more preferably about 30 to 50 patients are included in each arm of the study. Total study duration can be as short as one day to one week, but more preferably the study will run for 8 weeks to 12 weeks or up to 16 weeks or longer. The side effects can e.g. be assessed as the total number of times a certain side effect was reported in each group (irrespective of how many patients have experienced the side effect), or the side effects can be assessed as the number of patients that have experienced a certain side effect a certain number of times, such as at least once or at least twice or at least three times during the duration of the study. Furthermore, the severity of a side effect can be monitored, or a certain severity of a side effect can be required for it to qualify as a side effect in the study. A convenient way of assessing the severity of a side effect is via a visual analogue (VAS) scale.

Clinical Trial in Healthy Volunteers:

This study will typically be a single center study, following an open-label, randomized, crossover design to investigate the plasma concentrations, pharmacokinetics, safety and tolerability of pharmaceutical formulations according to the invention, possibly using the marketed formulation Fumaderm® as reference. The trial may be carried out as disclosed in detail in example 25 below.

In a further aspect, the formulation according to the invention—upon oral administration and in comparison to that obtained after oral administration of Fumaderm® tablets in an equivalent dosage—reduce flushing (frequency and/or severity).

In the present context the term "flushing" describes episodic attacks of redness of the skin together with a sensation of warmth or burning of the face and/or neck, and less frequently the upper trunk and abdomen or the whole body. It is the transient nature of the attacks that distinguishes flushing from the persistent erythema of photosensitivity or acute contact reactions. Repeated flushing over a prolonged period of time can lead to telangiectasia and occasionally to classical rosacea of the face (Greaves M W. Flushing and flushing syndromes, rosacea and perioral dermatitis. In: Champion R H, et al, eds. Rook/Wilkinson/Ebling textbook of dermatology, 6th ed., vol. 3. Oxford, UK: Blackwell Scientific, 1998: 2099-2104).

In the present context, a reduction of flushing is intended to denote a decrease in severity and/or incidence/frequency among a given treated patient population of flushing observed after administration of the formulation according to the invention compared with flushing observed after administration of Fumaderm® and can be measured e.g as described by O'toole et al. Cancer 2000, 88(4): p. 770-776. A reduction in flushing according to this definition could thus be construed as a reduction in incidence and/or severity of flushing. In one aspect of the invention, the incidence of flushing is reduced by at least about a quarter, in another aspect of the invention the incidence is reduced by at least about a third, in another aspect of the invention the incidence is reduced by at least about half, and in a further aspect of the invention, the flushing incidence is reduced by about two thirds or more. Likewise, the severity is in one aspect of the invention reduced by at least about a quarter, in another aspect of the invention by at least about a third, in another aspect of the invention by at least half, and in a further aspect of the invention by at least about two thirds. A one hundred percent reduction in flushing incidence and severity is most preferable, but is not required. The reduction of flushing, as described above, can be monitored in a clinical trial setting, e.g. comparing the administration of the compound according to the invention with e.g. administration of Fumaderm®. In case of a Fumaderm® controlled trial, the incidence and severity, defined as mild, moderate or severe, of flushing in the patients receiving the compound according to the invention compared to the Fumaderm® group, can be compared.

In one aspect, the severity of flushing is determined as the body surface area involved.

In one embodiment, such a clinical trial can be carried out as described above under "Clinical trial in patients". In another embodiment, such a clinical trial can be carried out as described above under "Clinical trial in healthy volunteers".

In a further aspect, the formulation according to the invention—upon oral administration and in comparison to that obtained after oral administration of Fumaderm® tablets in an equivalent dosage—reduce redness (frequency and/or severity).

In the present context the term "redness" describes episodic attacks of redness of the skin. In one aspect, the redness occurs in the face, neck, and less frequently the upper trunk and abdomen.

In the present context, a reduction of redness is intended to denote a decrease in severity and/or incidence/frequency among a given treated patient population of redness observed after administration of the formulation according to the invention compared with redness observed after administration of Fumaderm® and can e.g. be assessed by a clinician or nurse. A reduction in redness according to this definition could thus be construed as a reduction in incidence and/or severity of redness. In one aspect of the invention, the incidence of redness is reduced by at least about a quarter, in another aspect of the invention the incidence is reduced by at least about a third, in another aspect of the invention the incidence is reduced by at least about half, and in a further aspect of the invention, the redness incidence is reduced by about two thirds or more. Likewise, the severity is in one aspect of the invention reduced by at least about a quarter, in another aspect of the invention by at least about a third, in another aspect of the invention by at least half, and in a further aspect of the invention by at least about two thirds. A one hundred percent reduction in redness incidence and severity is most preferable, but is not required. The reduction of redness, as described above, can be monitored in a clinical trial setting, e.g. comparing the administration of the compound according to the invention with e.g. administration of Fumaderm®. In case of a Fumaderm® controlled trial, the incidence and severity, defined as mild, moderate or severe, of redness in the patients receiving the compound according to the invention compared to the Fumaderm® group, can be compared.

In one aspect, the severity of redness is determined as the body surface area involved.

In one embodiment, such a clinical trial can be carried out as described above under "Clinical trial in patients". In another embodiment, such a clinical trial can be carried out as described above under "Clinical trial in healthy volunteers".

In one embodiment, the relative bioavailability of the formulation of the invention compared to Fumaderm® is at least about 75%, such as at least about 80%, such as at least about 85%, such as at least about 90%, such as at least about 95%, such as about 100%.

In one embodiment, the relative bioavailability of the formulation of the invention compared to Fumaderm® is at least about 100%, such as at least about 110%, such as at least about 120%, such as at least about 125%, such as at least about 130%.

In one embodiment, the relative bioavailability of the formulation of the invention compared to Fumaderm® is at the most about 130%, such as at the most about 125%, such as at the most about 120%, such as at the most about 110%, such as at the most about 100%.

In the present context the term "erosion matrix" refers to a matrix wherein the release of the API does not depend upon intrinsic diffusion processes but rather is the result of the rate of the matrix erosion. By stripping off the erodible matrix layers in a well controlled manner, predetermined amounts of the API will be obtained, with the release of API being dependent on the rate of swelling and dissolution or erosion of the matrix and on the rate of dissolution, solubility and rate of diffusion of the API.

In an aspect the present invention relates to a pharmaceutical formulation comprising an erosion matrix which comprises:
  i) 10% to 80%, such as 20% to 70%, such as 20% to 60%, such as 30% to 60%, such as 35% to 60%, such as 35% to 55%, such as 40% to 55%, such as 44% to 55%, such as 40% to 50%, such as 42% to 48% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and
  ii) 1% to 50% by weight of one or more rate-controlling agents;
wherein erosion of said erosion matrix permits controlled or sustained release of said active substance In an aspect the present invention relates to a pharmaceutical formulation comprising an erosion matrix which comprises:
  i) 30% to 60%, such as 35% to 60%, such as 35% to 55%, such as 40% to 55%, such as 40% to 50%, such as 44% to 55%, such as 42% to 48% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and ii) 3% to 40% by weight of one or more rate-controlling agents;

wherein erosion of said erosion matrix permits controlled or sustained release of said active substance.

In some embodiments of the invention, it has been found that it is possible to obtain sustained release with a relatively low amount of rate-controlling agent while still obtaining sufficient drug exposure in the narrow window of absorption available in the small intestine, and thereby providing favourable pharmaco-kinetic properties, such as adequate relative bioavailability c.f. e.g. the prior art Fumaderm® formulation.

In some further embodiments, it has been found that it is possible to obtain enteric coated sustained release formulations according to the invention while still obtaining sufficient drug exposure in the narrow window of absorption available in the small intestine, and thereby providing favourable pharmaco-kinetic properties, such as adequate relative bioavailability c.f. e.g. the prior art Fumaderm® formulation.

In an aspect of the invention, the rate-controlling agent is a water-soluble polymer.

As used herein, the term "water-soluble polymer" means a conventional polymer for pharmaceutical use, having a solubility of more than 10 mg/ml in water. Suitable water-soluble polymers includes, but are not limited too, for example, hydroxypropylmethyl cellulose, hydroxypropyl cellulose, methyl cellulose and carboxymethyl cellulose. In one aspect, the water-soluble polymer is hydroxypropyl cellulose.

As used herein, the term "water-insoluble polymer" means a conventional polymer for pharmaceutical use, having a solubility of not more than 10 mg/ml in water.

In a further aspect of the invention, the erosion matrix contains essentially no water-insoluble polymer. In yet a further aspect, the erosion matrix contains no water-insoluble polymer.

In the present context the term "essentially no" refers to a level of less than about 1%, such as less than about 0.5%, such as less than about 0.3%, such as about 0.0%.

In an aspect of the invention, the rate-controlling agent is a water-soluble polymer and the erosion matrix contains essentially no water-insoluble polymer.

In an aspect of the invention, the rate-controlling agent is a water-soluble polymer and the erosion matrix contains no water-insoluble polymer.

In an embodiment of the invention, the rate-controlling agent is a cellulose polymer or a cellulose derivative or a mixture thereof. As non-limiting examples of a cellulose polymer or a cellulose derivative or a mixture thereof may be mentioned hydroxypropyl cellulose, hydroxypropyl methyl cellulose (HPMC), methyl cellulose, carboxymethyl cellulose and mixtures thereof.

In an embodiment of the invention the rate-controlling agent is hydroxypropyl cellulose. Many different grades of hydroxypropyl cellulose exist depending on e.g. the molecular weight thereof, the degree of etherification, viscosity etc. Non-limiting exemplary embodiments of commercially available hydroxypropyl celluloses are obtainable from e.g. Aqualon or Nippon Soda under the trade names Klucel® HPC-L, HPC-SL, HPC-SSL, HPC-M, HPC-H etc. In an embodiment of the invention, the rate-controlling agent is hydroxypropyl cellulose having a viscosity (mPa·s) of 3.0-5.9 as measured in an aqueous solution containing 2% by weight of dry HPC at 20° C. In an embodiment of the invention, the rate-controlling agent is HPC-SL.

In an embodiment of the invention the rate-controlling agent is present in an amount of 1-40% by weight, such as about 3-35% by weight, such as about 4-15% by weight, such as about 4-10% by weight, such as about 3-15% by weight, such as about 3-10% by weight, such as about 3-6% by weight, such as about 3-5.5% by weight, such as about 4-6% by weight.

In an embodiment of the invention the rate-controlling agent is present in an amount of 1-40% by weight, such as 3-35% by weight, such as 4-15% by weight, such as 4-10% by weight, such as 3-15% by weight, such as 3-10% by weight, such as 3-6% by weight, such as 3-5.5% by weight, such as 4-6% by weight.

In another embodiment of the invention, the rate-controlling agent is present in an amount of 15-40% by weight, such as about 15-25% by weight.

In another embodiment of the invention, the rate-controlling agent is present in an amount of about 25-40% by weight, such as about 35-40% by weight.

In another embodiment of the invention, the rate-controlling agent is present in an amount of about 0-5% by weight, such as about 0-3% by weight, such as in substantial absence of any rate-controlling agent.

In an aspect, the present invention relates to a pharmaceutical formulation comprising an erosion matrix which comprises:

i) 10% to 80%, such as 20% to 70%, such as 20% to 60%, such as 30% to 60%, such as 35% to 60%, such as 35% to 55%, such as 40% to 55%, such as 40% to 50%, such as 44% to 55%, such as 42% to 48%, by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance; and ii) 0% to 40%, such as 0% to 20%, such as 0% to 10%, such as 0% to 5%, such as 0% to 1%, by weight of one or more rate-controlling agents;

wherein erosion of said erosion matrix permits controlled release of said active substance.

The amount, if any, of rate-controlling agent varies in accordance with the specific rate-controlling agent used, the release profile aimed at, the level and nature of any excipients and additives present in the core tablet, etc.

In an embodiment of the invention the formulation further comprises a binder. Non-limiting examples thereof include water-soluble sugars and sugar alcohols, such as lactose, saccharose, glucose, sorbitol, mannitol etc. In an embodiment thereof, said binder is lactose. Lactose is commercially available in a number of different grades depending i.a. on the manufacturing method used resulting in a range of particle sizes, particle size distributions etc. Examples of lactose include, but are not limited to anhydrous lactose, lactose made from alpha-lactose-monohydrate, agglomerated lactose, granulated lactose, crystalline lactose, crystalline, sieved lactose, sieved lactose (e.g. PrismaLac®, such as PrismaLac® 40), crystalline, abrasive lactose (e.g. GranuLac®, such as GranuLac® 70, GranuLac® 140, GranuLac® 200, GranuLac® 230 and GranuLac® 400), improved lactose, agglomerated lactose (e.g. Tablettose®, such as Tablettose® 70, Tablettose® 80 and Tablettose® 100), improved lactose, spraydried lactose (FlowLac®, such as FlowLac® 90 and FlowLac® 100). Lactose is available from e.g. Meggle Pharma under the trade names PrismaLac®, Capsulac®, such as Capsulac®60, SacheLac®, SpheroLac®, Inhalac® GranuLac®, such as GranuLac® 70, GranuLac® 140, GranuLac® 200, GranuLac® 230 and GranuLac® 400, SorboLac®, Tablettose®, such as Tablettose® 70, Tablettose® 80 and Tablettose® 100, FlowLac®, such as FlowLac® 90 and FlowLac® 100.

In one aspect, the lactose is agglomerated lactose. In another aspect, the lactose is spraydried lactose. In another aspect, the lactose is abrasive lactose.

In an embodiment of the invention, the formulation according to the invention comprises:
i) 40% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 4-6% by weight of a rate-controlling agent;
iii) 35-55% by weight of a binder.

In an embodiment of the invention, the formulation according to the invention comprises:
i) 40% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 15-50% by weight of a rate-controlling agent;
iii) 5-30% by weight of a binder.

In an embodiment of the invention, the formulation according to the invention comprises:
i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 35-65% by weight of binder.

In an embodiment of the invention, the formulation according to the invention comprises:
i) 35% to 55% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 40-60% by weight of binder.

In an embodiment of the invention, the formulation according to the invention comprises:
i) 40% to 50% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 45-55% by weight of binder.

In an embodiment of the invention, the formulation according to the invention comprises:
i) 42% to 48% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-5.5% by weight of rate-controlling agent;
iii) 45-52% by weight of binder.

In an embodiment of the invention, the formulation according to the invention comprises:
i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 35-65% by weight of binder;
iv) 0.15-0.7% by weight of lubricant;
and optionally 0.05-0.25% by weight of flow control agents.

In an embodiment of the invention, the formulation according to the invention comprises:
i) 35% to 55% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 40-60% by weight of binder;
iv) 0.15-0.7% by weight of lubricant;
and optionally 0.05-0.25% by weight of flow control agents.

In an embodiment of the invention, the formulation according to the invention comprises:
i) 40% to 50% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-6% by weight of rate-controlling agent;
iii) 45-55% by weight of binder;
iv) 0.15-0.7% by weight of lubricant;
and optionally 0.05-0.25% by weight of flow control agents.

In an embodiment of the invention, the formulation according to the invention comprises:
i) 42% to 48% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
ii) 3-5.5% by weight of rate-controlling agent;
iii) 45-52% by weight of binder;
iv) 0.2-0.5% by weight of lubricant;
and optionally 0.05-0.2% by weight of flow control agents.

In an embodiment of the invention, the formulation according to the invention comprises:
i) 30% to 60% by weight of dimethyl fumarate;
ii) 3-6% by weight of HPC;
iii) 35-65% by weight of lactose.

In an embodiment of the invention, the formulation according to the invention comprises:
i) 35% to 55% by weight of dimethyl fumarate;
ii) 3-6% by weight of HPC;
iii) 40-60% by weight of lactose.

In an embodiment of the invention, the formulation according to the invention comprises:
i) 40% to 50% by weight of dimethyl fumarate;
ii) 3-6% by weight of HPC;
iii) 45-55% by weight of lactose.

In an embodiment of the invention, the formulation according to the invention comprises:
i) 42% to 48% by weight of dimethyl fumarate;
ii) 3-5.5% by weight of HPC;
iii) 45-52% by weight of lactose.

In an embodiment of the invention, the formulation according to the invention comprises:
i) 30% to 60% by weight of dimethyl fumarate;
ii) 3-6% by weight of HPC;
iii) 35-65% by weight of lactose;
iv) 0.15-0.7% by weight of magnesium stearate;
and optionally 0.05-0.25% by weight of silicon dioxide.

In an embodiment of the invention, the formulation according to the invention comprises:
i) 35% to 55% by weight of dimethyl fumarate;
ii) 3-6% by weight of HPC;
iii) 40-60% by weight of lactose;
iv) 0.15-0.7% by weight of magnesium stearate;
and optionally 0.05-0.25% by weight of silicon dioxide.

In an embodiment of the invention, the formulation according to the invention comprises:

i) 40% to 50% by weight of dimethyl fumarate;
ii) 3-6% by weight of HPC;
iii) 45-55% by weight of lactose;
iv) 0.15-0.7% by weight of magnesium stearate;
and optionally 0.05-0.25% by weight of silicon dioxide.

In an embodiment of the invention, the formulation according to the invention comprises:
i) 42% to 48% by weight of dimethyl fumarate;
ii) 3-5.5% by weight of HPC;
iii) 45-52% by weight of lactose;
iv) 0.2-0.5% by weight of magnesium stearate;
and optionally 0.05-0.2% by weight of silicon dioxide.

In an embodiment of the invention, the formulation according to the invention comprises:
A) A tablet core consisting of:
i) 30% to 60% by weight of dimethyl fumarate as an active substance having a particle size distribution such that 0-5% of the particles have a particle size>500 μm and 45-53% of the particles have a particle size>250 μm, and 7-15% of the particles have a particle size<100 μm;
ii) 3-6% by weight of HPC;
iii) 35-65% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 35% to 55% by weight of dimethyl fumarate as an active substance having a particle size distribution such that 0-5% of the particles have a particle size>500 μm and 45-53% of the particles have a particle size>250 μm, and 7-15% of the particles have a particle size<100 μm;
ii) 3-6% by weight of HPC;
iii) 40-60% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 40% to 50% by weight of dimethyl fumarate as an active substance having a particle size distribution such that 0-5% of the particles have a particle size>500 μm and 45-53% of the particles have a particle size>250 μm, and 7-15% of the particles have a particle size<100 μm;
ii) 3-6% by weight of HPC;
iii) 45-55% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 42% to 48% by weight of dimethyl fumarate as an active substance having a particle size distribution such that 0-5% of the particles have a particle size>500 μm and 45-53% of the particles have a particle size>250 μm, and 7-15% of the particles have a particle size<100 μm;
ii) 3-5.5% by weight of HPC;
iii) 45-52% by weight of lactose;
iv) 0.2-0.5% by weight of magnesium stearate and 0.05-0.2% by weight of silicon dioxide; and
B) an enteric coating in an amount of about 1.5-3.5% by weight of the core.

In an embodiment of the invention, the formulation according to the invention comprises:
A) A tablet core consisting of:
i) 30% to 60% by weight of dimethyl fumarate as an active substance having a particle size distribution such that 0-7% of the particles have a particle size>500 μm and 42-59% of the particles have a particle size>250 μm, and 3-12% of the particles have a particle size<100 μm;
ii) 3-6% by weight of HPC;
iii) 35-65% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 35% to 55% by weight of dimethyl fumarate as an active substance having a particle size distribution such that 0-7% of the particles have a particle size>500 μm and 42-59% of the particles have a particle size>250 μm, and 3-12% of the particles have a particle size<100 μm;
ii) 3-6% by weight of HPC;
iii) 40-60% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 40% to 50% by weight of dimethyl fumarate as an active substance having a particle size distribution such that 0-7% of the particles have a particle size>500 μm and 42-59% of the particles have a particle size>250 μm, and 3-12% of the particles have a particle size<100 μm;
ii) 3-6% by weight of HPC;
iii) 45-55% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 42% to 48% by weight of dimethyl fumarate as an active substance having a particle size distribution such that 0-7% of the particles have a particle size>500 μm and 42-59% of the particles have a particle size>250 μm, and 3-12% of the particles have a particle size<100 μm;
ii) 3-5.5% by weight of HPC;
iii) 45-52% by weight of lactose;
iv) 0.2-0.5% by weight of magnesium stearate and 0.05-0.2% by weight of silicon dioxide; and
B) an enteric coating in an amount of about 1.5-3.5% by weight of the core.

In an embodiment of the invention, the formulation according to the invention comprises:
A) A tablet core consisting of:
i) 30% to 60% by weight of dimethyl fumarate as an active substance having a particle size distribution such that 0-10% of the particles have a particle size>500 μm and 40-65% of the particles have a particle size>250 μm, and 2-10% of the particles have a particle size<100 μm;
ii) 3-6% by weight of HPC;

iii) 35-65% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 35% to 55% by weight of dimethyl fumarate as an active substance having a particle size distribution such that 0-10% of the particles have a particle size>500 μm and 40-65% of the particles have a particle size>250 μm, and 2-10% of the particles have a particle size<100 μm;
ii) 3-6% by weight of HPC;
iii) 40-60% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 40% to 50% by weight of dimethyl fumarate as an active substance having a particle size distribution such that 0-10% of the particles have a particle size>500 μm and 40-65% of the particles have a particle size>250 μm, and 2-10% of the particles have a particle size<100 μm;
ii) 3-6% by weight of HPC;
iii) 45-55% by weight of lactose;
iv) 0.15-0.7% by weight of magnesium stearate and 0.05-0.25% by weight of silicon dioxide; and
B) an enteric coating in an amount of about 1.5-3.5% by weight of the core.

In an embodiment of the invention, the formulation according to the invention comprises:
A) A tablet core consisting of:
i) 42% to 48% by weight of dimethyl fumarate as an active substance having a particle size distribution such that 0-10% of the particles have a particle size>500 μm and 40-65% of the particles have a particle size>250 μm, and 2-10% of the particles have a particle size<100 μm;
ii) 3-5.5% by weight of HPC;
iii) 45-52% by weight of lactose;
iv) 0.2-0.5% by weight of magnesium stearate and 0.05-0.2% by weight of silicon dioxide; and
B) an enteric coating in an amount of about 1.5-3.5% by weight of the core.

In an embodiment the formulation according to the invention further comprises one or more lubricants.

In an embodiment the formulation according to the invention further comprises one or more flow control agents.

In an embodiment the formulation according to the invention further comprises one or more lubricants and one or more flow control agents.

In an embodiment the formulation according to the invention further comprises pharmaceutically acceptable excipients and additives selected from the group comprising lubricants, glidants, disintegrants, flow control agents, solubilizers, pH control agents, surfactants and emulsifiers.

In an embodiment, the formulation according to the invention is manufactured without the use of a disintegrant.

Some of the formulations according to the invention show bi-phasic in vitro dissolution profiles, wherein the release of the API such as dimethyl fumarate is slower while in the acidic environment of the first two hours of a USP dissolution apparatus, and faster once the dissolution medium is changed to pH 6.8, even though the solubility of the API may be the same in acid and alkaline environment. For drugs where a relatively low exposure to the stomach is desired, but at the same time requiring release/absorption in the small intestine it will thereby be possible to limit the exposure of the API to the stomach while optimising the exposure of the API to the small intestine. In an embodiment the in vitro dissolution profile of the formulation is bi-phasic i.e. the release of the API is slower while in the acidic environment of the first two hours of a USP dissolution apparatus, and faster once the dissolution medium is changed to pH 6.8.

The in vitro dissolution rate describes how the amount released of the API contained in a formulation according to the invention—when subjected to an in vitro dissolution test—changes over time. A higher/faster in vitro dissolution rate means that a larger amount of the API is released over a certain period of time, and a lower/slower in vitro dissolution rate means that a smaller amount of the API is released over the same period of time—when subjected to the same in vitro dissolution testing conditions.

In an embodiment of the invention, the in vitro dissolution test used for determining the in vitro dissolution rate employs 0.1 N hydrochloric acid as dissolution medium during the first 2 hours of the test and then 0.05 M phosphate buffer pH 6.8 as dissolution medium.

In an embodiment of the invention, the in vitro dissolution rate of the API contained in a non-enteric coated formulation according to the invention—when subjected to an in vitro dissolution test employing 0.1 N hydrochloric acid as dissolution medium during the first 2 hours of the test and then 0.05 M phosphate buffer pH 6.8 as dissolution medium—is higher in the buffer (pH 6.8) phase c.f. the acid phase (0.1 N hydrochloric acid as dissolution medium) of the in vitro dissolution test, such as at least 10% higher, such as at least 20% higher, such as at least 30% higher, such as at least 40% higher, such as at least 50% higher, such as at least 60% higher, such as at least 70% higher, such as at least 80% higher, such as at least 90% higher, such as at least 100% higher, such as at least 125% higher, such as at least 150% higher, such as at least 200% higher, such as at least 250% higher, such as at least 300% higher, such as at least 350% higher, such as at least 400% higher in the buffer (pH 6.8) phase c.f. the acid phase (0.1 N hydrochloric acid as dissolution medium) of the in vitro dissolution test. In an embodiment the comparison is made between the in vitro dissolution rate during the first hour of the test (between time=0 and time=1 hour) and the in vitro dissolution rate in the third hour (between time=2 hours and time=3 hours) of the test. In another embodiment the comparison is made between the in vitro dissolution rate during the first two hours of the test (between time=0 and time=2 hours) and the in vitro dissolution rate in the third hour (between time=2 hours and time=3 hours) of the test. In another embodiment the comparison is made between the in vitro dissolution rate during the first two hours of the test (between time=0 and time=2 hours) and the in vitro dissolution rate in the subsequent two hours (between time=2 hours and time=4 hours) of the test. In another embodiment the comparison is made between the in vitro dissolution rate during the first hour of the test (between time=0 and time=1 hour) and the in vitro dissolution rate between time=2 hours and time=2.5 hours of the test.

In an embodiment the formulation according to the invention further comprises one or more coatings. In an embodiment of the invention said one or more coatings are added in order to improve stability and swallowing characteristics of the tablets or to delay release of the API. In an embodiment thereof said coatings are film coatings and/or enteric coatings. The film coating may improve swallowing characteristics as well as stability and can also mitigate the risk of sublimation of the active pharmaceutical ingredient. Furthermore, the film coating may improve the safety aspect of handling the tablets. A film coat with an overlying enteric coat, or an enteric coat by itself may have similar benefits to the ones listed above for film coating. However, in addition, the active pharmaceutical ingredient may not be released in the acidic environment of the gastric ventricle, potentially protecting the gastric mucosa from irritation, if the API has an irritant potential for the gastric mucosa.

In an embodiment of the invention said coating is an enteric coating.

Enteric coating materials may be selected from any of a number of commercially available coating materials. Non-limiting examples thereof include Eudragit® E, L, S, L30D55, Kollicoat® 30D, Cellulose Acetate Phthalate, Polyvinyl Acetate Phthalate, and Hypromellose Phthalate.

In an embodiment of the invention said enteric coating is applied at a level of about 1.0-5.0% by weight of the core.

In an embodiment of the invention said enteric coating is applied at a level of about 1.0-4.5% by weight of the core, such as 1.5-4.0% by weight of the core, such as about 1.5-3.5% by weight of the core, such as about 2.0-3.5% by weight of the core, such as about 2-3% by weight of the core.

In an embodiment of the invention said enteric coating is applied at a level of about 1.5-3.5% by weight of the core.

Enteric coating is a well established approach to prevent or minimise drug release in the stomach and allow release in the small intestine. Such enteric polymer coatings work on the principle of pH dependent solubility: insoluble in the low pH conditions of the stomach but soluble in the near neutral pH environment of the proximal small intestine having a pH in the range 5-6.

For drugs requiring absorption in the small intestine this leaves open only a narrow window of release, such as about 5 hours, such as about 4 hours, such as about 3 hours, such as about 2½ hours, such as about 2 hours between solubilisation of the enteric coating and release of the API from the formulation. In some embodiments of the invention, it has been found that rapid solubilisation of the enteric coating is possible by the application of a relatively thin coat while surprisingly still obtaining the required protection against the acid environment of the stomach as e.g. shown—when subjected to an in vitro dissolution test employing 0.1 N hydrochloric acid as dissolution medium during 2 hours—by less than 10%, such as less than 5%, such as less than 2%, such as about 0% release of the fumaric ester contained in the formulation.

In an embodiment of the invention the in vivo release of the fumaric acid ester displays an earlier onset of release than the prior art formulation Fumaderm®, such as at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, or at least 120 minutes earlier than Fumaderm® under fasting conditions.

In an embodiment of the invention, the formulation according to the invention comprises an enteric coating and the in vivo release of the fumaric acid ester displays an earlier onset of release than the prior art formulation Fumaderm®, such as at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, or at least 120 minutes earlier than Fumaderm® under fasting conditions.

In an embodiment of the invention the in vivo release of the fumaric acid ester displays a lag time of 15 minutes to 2 hours under fasting conditions, such as a lag time of at the most 120 minutes, at the most 110 minutes, at the most 100 minutes, at the most 90 minutes, at the most 80 minutes, at the most 70 minutes, at the most 60 minutes, at the most 50 minutes, at the most 40 minutes, at the most 30 minutes, at the most 20 minutes, or at the most 15 minutes under fasting conditions.

In an embodiment of the invention, the formulation according to the invention comprises an enteric coating and the in vivo release of the fumaric acid ester displays a lag time of 15 minutes to 2 hours under fasting conditions, such as a lag time of at the most 120 minutes, at the most 110 minutes, at the most 100 minutes, at the most 90 minutes, at the most 80 minutes, at the most 70 minutes, at the most 60 minutes, at the most 50 minutes, at the most 40 minutes, at the most 30 minutes, at the most 20 minutes, or at the most 15 minutes under fasting conditions.

In an embodiment of the invention, the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 50% w/w of the fumaric ester contained in the formulation is released, and/or within the first 3 hours after start of the test from about 20% w/w to about 75% w/w of the total amount of the fumaric acid ester contained in the formulation is released.

In an embodiment of the invention, the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 3.5 hours after start of the test at the most about 95% w/w of the total amount of the fumaric acid ester contained in the formulation is released.

In an embodiment of the invention, the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 4 hours after start of the test at the most about 98% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 60% w/w, such as about 0% w/w to about 50% w/w, such as about 0% w/w to about 40% w/w, such as about 0% w/w to about 30%, such as about 0% w/w to about 20%, such as about 0% w/w to about 10%, such as about 0% w/w to about 5%, such as about 0% w/w of the fumaric ester contained in the formulation is released, and/or within the first 3 hours after start of the test from about 15% w/w to about 95% w/w, such as about 20% w/w to about 95% w/w, such as about 20% w/w to about 75% w/w, such as about 25% w/w to about 75% w/w, such as about 40% w/w to about 95% w/w, such as about 40% w/w to about 75% w/w, such as about 50% w/w to about 95% w/w, such as about 50% w/w to about 75%, such as about 60% w/w to about 95% w/w, such as about 60% w/w to about 75%, such as about 70% w/w to about 95%, such as about 80% w/w to about 95%, such as about 90% w/w to about 95% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 60% w/w, such as about 0% w/w to about 5% w/w, such as about 0% w/w to about 10% w/w, or such as about 15% w/w to about 35% w/w, or such as about 35% w/w to about 55% w/w of the fumaric ester contained in the formulation is released, and/or
within the first 3 hours after start of the test from about 15% w/w to about 95% w/w, such as about 15% w/w to about 75% w/w, such as about 20% w/w to about 75% w/w, such as about 15% w/w to about 35% w/w, or such as about 35% w/w to about 55% w/w, or such as about 55% w/w to about 75%, or such as about 65% w/w to about 85%, or such as about 70% w/w to about 80%, or such as about 75% w/w to about 95%, or such as about 85% w/w to about 95% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 1% w/w to about 25% w/w of the fumaric ester contained in the formulation is released, and/or
within the first 3 hours after start of the test from about 15% w/w to about 95% w/w, such as about 15% w/w to about 75% w/w, such as about 25% w/w to about 95% w/w, such as about 25% w/w to about 75% w/w, such as about 40% w/w to about 95% w/w, such as about 40% w/w to about 75% w/w, such as about 50% w/w to about 95% w/w, such as about 50% w/w to about 75%, such as about 60% w/w to about 95% w/w, such as about 60% w/w to about 75%, such as about 70% w/w to about 95% w/w, such as about 80% w/w to about 95% w/w, such as about 90% w/w to about 95% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 1% w/w to about 25% w/w of the fumaric ester contained in the formulation is released, and/or
within the first 3 hours after start of the test from about 15% w/w to about 95% w/w, such as about 15% w/w to about 75% w/w, such as about 15% w/w to about 35% w/w, or such as about 35% w/w to about 55% w/w, or such as about 55% w/w to about 75%, or such as about 65% w/w to about 85%, or such as about 70% w/w to about 80%, or such as about 75% w/w to about 95%, or such as about 85% w/w to about 95% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 3.5 hours after start of the test at the most about 100% w/w, such as about 30% w/w to about 100% w/w, such as about 30% w/w to about 95% w/w, such as about 40% w/w to about 100% w/w, such as about 40% w/w to about 95% w/w, such as about 50% w/w to about 100% w/w, such as about 50% w/w to about 95%, such as about 60% w/w to about 100% w/w, such as about 60% w/w to about 95%, such as about 70% w/w to about 100% w/w, such as about 70% w/w to about 95%, such as about 80% w/w to about 100% w/w, such as about 80% w/w to about 95%, such as about 90% w/w to about 100% w/w, such as about 90% w/w to about 95% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 3.5 hours after start of the test at the most about 100% w/w, such as about 30% w/w to about 90% w/w, such as about 30% w/w to about 50% w/w, or such as about 60% w/w to about 80%, or such as about 80% w/w to about 95% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 4 hours after start of the test at the most about 100% w/w, such as about 35% w/w to about 100% w/w, such as about 35% w/w to about 98% w/w, such as about 40% w/w to about 100% w/w, such as about 40% w/w to about 98% w/w, such as about 50% w/w to about 100% w/w, such as about 50% w/w to about 98%, such as about 60% w/w to about 100% w/w, such as about 60% w/w to about 98%, such as about 70% w/w to about 100% w/w, such as about 70% w/w to about 98%, such as about 80% w/w to about 100% w/w, such as about 80% w/w to about 98%, such as about 90% w/w to about 100% w/w, such as about 90% w/w to about 98% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 4 hours after start of the test at the most about 100% w/w, such as about 35% w/w to about 98% w/w, such as about 50% w/w to about 70%, or such as about 85% w/w to about 95% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 4 hours after start of the test at the most about 95% w/w, such as at the most about 90% w/w, such as at the most about 70% of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 15% w/w to about 35% w/w of the total amount of the fumaric acid ester contained in the formulation is released; and
within the first 3.5 hours after start of the test from about 30% w/w to about 50% w/w of the total amount of the fumaric acid ester contained in the formulation is released; and
within the first 4 hours after start of the test from about 50% w/w to about 70% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 15% w/w to about 35% w/w of the total amount of the fumaric acid ester contained in the formulation is released; and
within the first 3.5 hours after start of the test from about 30% w/w to about 50% w/w of the total amount of the fumaric acid ester contained in the formulation is released; and
within the first 4 hours after start of the test from about 50% w/w to about 70% w/w of the total amount of the fumaric acid ester contained in the formulation is released; and
within the first 5 hours after start of the test from about 70% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 30% w/w to about 55% w/w of the total amount of the fumaric acid ester contained in the formulation is released; and
within the first 3.5 hours after start of the test from about 60% w/w to about 80% w/w of the total amount of the fumaric acid ester contained in the formulation is released; and
within the first 4 hours after start of the test from about 80% w/w to about 95% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 30% w/w to about 55% w/w of the total amount of the fumaric acid ester contained in the formulation is released; and
within the first 3.5 hours after start of the test from about 60% w/w to about 80% w/w of the total amount of the fumaric acid ester contained in the formulation is released; and
within the first 4 hours after start of the test from about 80% w/w to about 95% w/w of the total amount of the fumaric acid ester contained in the formulation is released; and
within the first 5 hours after start of the test from about 80% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 60% w/w to about 85% w/w of the total amount of the fumaric acid ester contained in the formulation is released; and
within the first 3.5 hours after start of the test from about 80% w/w to about 95% w/w of the total amount of the fumaric acid ester contained in the formulation is released; and
within the first 4 hours after start of the test from about 85% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 0% w/w to about 5% w/w of the total amount of the fumaric ester contained in the formulation is released, and
within the first 3 hours after start of the test from about 60% w/w to about 85% w/w of the total amount of the fumaric acid ester contained in the formulation is released; and
within the first 3.5 hours after start of the test from about 80% w/w to about 100% w/w of the total amount of the fumaric acid ester contained in the formulation is released; and
within the first 4 hours after start of the test from about 85% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
within the first 2 hours after start of the test from about 15% w/w to about 35% w/w of the fumaric ester contained in the formulation is released, and
within the first 3 hours after start of the test from about 55% w/w to about 80% w/w of the total amount of the fumaric acid ester contained in the formulation is released; and
within the first 3.5 hours after start of the test from about 70% w/w to about 90% w/w of the total amount of the fumaric acid ester contained in the formulation is released; and
within the first 4 hours after start of the test from about 80% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 10% w/w to about 30% w/w of the total amount of the fumaric acid ester contained in the formulation is released; and within the first 3.5 hours after start of the test from about 15% w/w to about 40% w/w of the total amount of the fumaric acid ester contained in the formulation is released; and within the first 4 hours after start of the test from about 30% w/w to about 50% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 10% w/w to about 30% w/w of the total amount of the fumaric acid ester contained in the formulation is released; and within the first 3.5 hours after start of the test from about 15% w/w to about 40% w/w of the total amount of the fumaric acid ester contained in the formulation is released; and within the first 4 hours after start of the test from about 30% w/w to about 50% w/w of the total amount of the fumaric acid ester contained in the formulation is released; and within the first 6 hours after start of the test from about 75% w/w to about 100% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 5% w/w to about 25% w/w of the total amount of the fumaric acid ester contained in the formulation is released; and within the first 3.5 hours after start of the test from about 10% w/w to about 30% w/w of the total amount of the fumaric acid ester contained in the formulation is released; and within the first 4 hours after start of the test from about 20% w/w to about 40% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 5% w/w to about 25% w/w of the total amount of the fumaric acid ester contained in the formulation is released; and within the first 3.5 hours after start of the test from about 10% w/w to about 30% w/w of the total amount of the fumaric acid ester contained in the formulation is released; and within the first 4 hours after start of the test from about 20% w/w to about 40% w/w of the total amount of the fumaric acid ester contained in the formulation is released; and within the first 5 hours after start of the test from about 30% w/w to about 50% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 2% w/w to about 20% w/w of the total amount of the fumaric acid ester contained in the formulation is released; and within the first 3.5 hours after start of the test from about 5% w/w to about 20% w/w of the total amount of the fumaric acid ester contained in the formulation is released; and within the first 4 hours after start of the test from about 5% w/w to about 25% w/w of the total amount of the fumaric acid ester contained in the formulation is released.

In an embodiment of the invention the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:

within the first 2 hours after start of the test from about 0% w/w to about 5% w/w of the total amount of the fumaric ester contained in the formulation is released, and within the first 3 hours after start of the test from about 2% w/w to about 20% w/w of the total amount of the fumaric acid ester contained in the formulation is released; and within the first 3.5 hours after start of the test from about 5% w/w to about 20% w/w of the total amount of the fumaric acid ester contained in the formulation is released; and within the first 4 hours after start of the test from about 5% w/w to about 25% w/w of the total amount of the fumaric acid ester contained in the formulation is released; and within the first 5 hours after start of the test from about 10% w/w to about 30% w/w of the total amount of the fumaric acid ester contained in the formulation is released.

In an embodiment of the invention the release has zero order, first order or square-root (Higuchi's) kinetics release profile.

In a further embodiment the in vitro release has a combination of zero order, first order and square-root (Higuchi's) kinetics in vitro release profiles, e.g. a combination of zero and first order in vitro release profiles.

Different kinetic models, such as zero-order (1), first-order (2), square-root (Higuchi's equation) (3) can be applied to the interpretation of the drug release kinetic.

$$M_t = M_0 + k_0 * t \qquad 1:$$

$$\ln M_t = \ln M + k_1 * t \qquad 2:$$

$$M_t = M_0 + k_H * t^{1/2} \qquad 3:$$

In these equations, $M_t$ is the cumulative amount of drug released at any specified time point and $M_0$ is the dose of active substance incorporated in the pharmaceutical composition. $k_0$, $k_1$ and $k_H$ are rate constants for zero-order, first-order and Higuchi's equation, respectively.

One aspect of the invention relates to a zero-order dissolution release profile. Another aspect relates to a first-order dissolution release profile. A further aspect relates to a square-root (Higuchi's equation) dissolution release profile.

The active substance in a formulation of the invention is any fumaric acid ester.

In one embodiment of the invention the fumaric acid ester is preferably selected from the group consisting of dimethylfumarate, diethylfumarate, dipropylfumarate, dibutylfumarate, dipentylfumarate, methyl-ethylfumarate, methyl-propylfumarate, methyl-butylfumarate, methyl-pentylfumarate, monomethylfumarate, monoethylfumarate, monopropylfumarate, monobutylfumarate and monopentylfumarate, including pharmaceutically acceptable salts thereof.

Pharmaceutically acceptable salts thereof comprise metal salts, such as a salt selected from alkali metal salts and alkaline earth metal salts including sodium, potassium, calcium, magnesium, strontium or zinc salts, amino acid salts etc.

In another embodiment of the invention the fumaric acid ester is present in the form of a monosaccharide ester thereof such as e.g. described in EP06753340.6.

In another embodiment of the invention the fumaric acid ester is present in the form of an amino acid salt thereof. The amino acid may be a naturally occurring amino acid such as glycine, alanine, valine, norvaline, isovaline, leucine, norleucine, isoleucine, methionine, phenylalanine, tryptophan, serine, thereonine, cysteine, penicillamine, tyrosine, asparagine, glutamine, aspartic acid, glutamic acid, ornithine, lysine, arginine, histidine, proline, 4-hydroxproline and pipecolic acid.

In a specific embodiment of the invention, the fumaric acid ester is a mono-$(C_1-C_5)$alkylester of fumaric acid that is present in the form of a pharmaceutically acceptable salt. Suitable salts are e.g. metal salts such as a salt selected from alkali metal salts and alkaline earth metal salts including sodium, potassium, calcium, magnesium, strontium or zinc salt.

The term $(C_1-C_5)$ alkyl refers to a branched or un-branched alkyl group having from one to five carbon atoms inclusive, such as methyl, ethyl, 1-propyl, 2-propyl, 1-butyl, 2-butyl, 2-methyl-2-propyl, 2-methyl-1-propyl and pentyl.

In another embodiment, the formulation according to the invention comprises dimethylfumarate as the active substance.

In a further embodiment, the formulation according to the invention comprises monomethylfumarate as the active substance optionally in the form of a pharmaceutically acceptable salt like e.g. its sodium, potassium, calcium, magnesium, strontium and/or zinc salt.

In a further embodiment, the formulation according to the invention comprises monomethylfumarate as the active substance optionally in the form of an amino acid salt thereof.

In another embodiment, the formulation according to the invention consists essentially of dimethylfumarate as the active substance.

In another embodiment, the formulation according to the invention consists of dimethylfumarate as the active substance.

In a further embodiment, the formulation according to the invention consists essentially of monomethylfumarate as the active substance optionally in the form of a pharmaceutically acceptable salt like e.g. its sodium, potassium, calcium, magnesium, strontium and/or zinc salt.

In a further embodiment, the formulation according to the invention consists of monomethylfumarate as the active substance optionally in the form of a pharmaceutically acceptable salt like e.g. its sodium, potassium, calcium, magnesium, strontium and/or zinc salt.

In a further embodiment, the formulation according to the invention comprises dimethylfumarate and monomethylfumarate (optionally in the form of a pharmaceutically acceptable salt like e.g. its sodium, potassium, calcium, magnesium, strontium and/or zinc salt) as the active substances, in a weight ratio between about 1:10 and about 10:1.

In a further embodiment, the formulation according to the invention consists essentially of dimethylfumarate and monomethylfumarate (optionally in the form of a pharmaceutically acceptable salt like e.g. its sodium, potassium, calcium, magnesium, strontium and/or zinc salt) as the active substances, in a weight ratio between about 1:10 and about 10:1.

In a further embodiment, the formulation according to the invention consists of dimethylfumarate and monomethylfumarate (optionally in the form of a pharmaceutically acceptable salt like e.g. its sodium, potassium, calcium, magnesium, strontium and/or zinc salt) as the active substances, in a weight ratio between about 1:10 and about 10:1.

In an embodiment the formulation according to the invention is for administration once, twice or three times daily.

In an embodiment the formulation is for administration once daily.

In an embodiment the formulation is for administration twice daily.

The daily dosage of the controlled release pharmaceutical formulation according to the invention that is administered to treat a patient depends on a number of factors among which are included, without limitation, weight and age and the underlying causes of the condition or disease to be treated, and is within the skill of a physician to determine.

In one aspect of the invention the daily dosage can be e.g. from 200 to 400 mg active substance given in one to three doses, in another aspect from 300 to 500 mg active substance given in one to three doses, in another aspect 400 to 600 mg active substance given in one to three doses, in another aspect 500 to 700 mg active substance given in one to three doses, in another aspect 600 to 800 mg active substance given in one to three doses, in another aspect 700 to 900 mg active substance given in one to three doses, in another aspect 800 to 1000 mg active substance given in one to three doses, in another aspect 900 to 1100 mg active substance given in one to three doses, in another aspect 1000 to 1200 mg active substance given in one to three doses, in another aspect 1100 to 1300 mg active substance given in one to three doses, in another aspect 1200 to 1400 mg active substance given in one to three doses and in yet another aspect 1300 to 2000 mg active substance given in one to three doses.

An embodiment of the invention is a pharmaceutical formulation comprising:
i) 40% to 55% by weight of dimethyl fumarate;
ii) 4-6% by weight of hydroxypropyl cellulose;
iii) 35-55% by weight of lactose.

An embodiment of the invention is a pharmaceutical formulation comprising:
i) 30% to 60% by weight of dimethyl fumarate;
ii) 3-6% by weight of hydroxypropyl cellulose;
iii) 35-65% by weight of lactose.

An embodiment of the invention is a pharmaceutical formulation in the form of an erosion matrix tablet comprising:
A) A tablet core comprising:
i) 40-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 4-6% by weight of a rate-controlling agent;
iii) 35-55% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

An embodiment of the invention is a pharmaceutical formulation in the form of an erosion matrix tablet comprising:
A) A tablet core comprising:
i) 30-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 3-6% by weight of a rate-controlling agent;
iii) 35-65% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

An embodiment of the invention is a pharmaceutical formulation in the form of a monolithic erosion matrix tablet comprising:
A) A tablet core comprising:
i) 40-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 4-6% by weight of a rate-controlling agent;
iii) 35-55% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

An embodiment of the invention is a pharmaceutical formulation in the form of a monolithic erosion matrix tablet comprising:
A) A tablet core comprising:
i) 30-60% by weight of one or more fumaric acid esters selected from di-$(C_1-C_5)$alkylesters of fumaric acid and mono-$(C_1-C_5)$alkylesters of fumaric acid, or a pharmaceutically acceptable salt thereof, as an active substance,
ii) 3-6% by weight of a rate-controlling agent;
iii) 35-65% by weight of a binder;
B) an enteric coating in an amount of about 1.5-3.5% by weight of the core;
wherein erosion of said erosion matrix results in release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the fumaric ester contained in the formulation is released, and/or
within the first 3 hours after start of the test from about 20% w/w to about 75% w/w of the fumaric ester contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the fumaric acid ester contained in the formulation is released.

An embodiment of the invention is a pharmaceutical formulation in the form of an erosion matrix tablet comprising:
A) A tablet core comprising:
i) 40-55% by weight of dimethyl fumarate,
ii) 4-6% by weight of hydroxypropyl cellulose;
iii) 35-55% by weight of lactose;
B) an enteric coating in an amount of about 1.5-3.5% by weight of the core;
wherein erosion of said erosion matrix results in release of the dimethyl fumarate—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the dimethyl fumarate contained in the formulation is released, and/or
within the first 3 hours after start of the test from about 20% w/w to about 75% w/w of the dimethyl fumarate contained in the formulation is released, and/or within the first 4 hours after start of the test from about 50% w/w to about 98% w/w of the fumaric ester contained in the formulation is released, and/or
within the first 5 hours after start of the test from about 70% w/w to about 100% w/w of the total amount of the dimethyl fumarate contained in the formulation is released.

An embodiment of the invention is a pharmaceutical formulation in the form of a monolithic erosion matrix tablet comprising:
A) A tablet core comprising:
  i) 40-55% by weight of dimethyl fumarate,
  ii) 4-6% by weight of hydroxypropyl cellulose;
  iii) 35-55% by weight of lactose;
B) an enteric coating in an amount of about 1.5-3.5% by weight of the core;
wherein erosion of said erosion matrix results in release of the dimethyl fumarate—when subjected to an in vitro dissolution test employing 0.1 N hydrochloric acid as dissolution medium during the first 2 hours of the test and then 0.05 M phosphate buffer pH 6.8 as dissolution medium—as follows:
within the first 2 hours after start of the test from about 0% w/w to less than about 10% w/w of the dimethyl fumarate contained in the formulation is released, and/or
within the first 3 hours after start of the test from about 20% w/w to about 75% w/w of the dimethyl fumarate contained in the formulation is released, and/or
within the first 4 hours after start of the test from about 50% w/w to about 98% w/w of the fumaric ester contained in the formulation is released, and/or
within the first 5 hours after start of the test from about 70% w/w to about 100% w/w of the total amount of the dimethyl fumarate contained in the formulation is released.

Preparation of the erosion matrix tablets according to the invention may be obtained by granulation, followed by tabletting and optionally film and/or enteric coating of the core tablets obtained. The core can for example be made by conventional wet granulation or continuous granulation such as extrusion followed by compaction of the granules into tablets. The core may then be coated using an appropriate technology, preferably by air suspension.

An aspect of the invention is a method for preparing the formulation according to the invention, comprising the steps of:
a) Dissolving (or suspending) either one or both of a fumaric acid ester and optionally a rate-controlling agent in the form of a polymeric matrix material in water to obtain an aqueous suspension thereof;
b) Spraying said aqueous suspension on granules of a fumaric acid ester and/or a binder for a period of time sufficient to obtain a uniform coating thereon;
c) Drying the granules obtained;
d) Optionally sieving or milling said granules;
e) Blending of any pharmaceutically acceptable excipients and additives in a manner known per se to obtain a tablet formulation;
f) Optionally film and/or enteric coating of said tablet formulation in a manner known per se;
wherein any of or all of the above steps are performed at a temperature to allow a product temperature not exceeding 45° C. In an embodiment of the invention any of or all of the above steps are performed at a temperature to allow a product temperature not exceeding 40° C., such as not exceeding 35° C., such as not exceeding 30° C. Thus it has surprisingly been shown that the preparation of the formulation according to the invention may be obtained by the use of solely water as solvent, thus obviating the need for any organic solvents. Furthermore all process steps may be carried out at a rather low temperature. Thereby any sublimation of the active pharmaceutical ingredient is minimised or reduced and an energy-efficient process is obtained, mitigating loss of API, thus reducing cost as well as improving environmental and workers' safety.

In the present context particle size is measured by conventional sieve analysis known to the person skilled in the art.

In an embodiment of the invention the fumaric acid ester is micronized to obtain a particle size, wherein at least 90% of the particles have a particle size of at most 50 μm, such as at most 30 μm, such as at most 10 μm, prior to step a) above.

In another embodiment, the mean particle size of the active pharmaceutical ingredient (the fumaric acid ester(s)) is reduced, e.g. by sieving or milling, such that at least 50% of the particles have a particle size of less than 800 μm, such as less than 600 μm, such as less than 500 μm, such as less than 400 μm, such as less than 200 μm, prior to step a) above.

In another embodiment, the mean particle size of the active pharmaceutical ingredient (the fumaric acid ester(s)) is reduced, e.g. by sieving or milling, such that at least 80% of the particles have a particle size of less than 800 μm, such as less than 600 μm, such as less than 500 μm, such as less than 400 μm, such as less than 200 μm, prior to step a) above.

In another embodiment, the mean particle size of the active pharmaceutical ingredient (the fumaric acid ester(s)) is reduced, e.g. by sieving or milling, such that at least 90% of the particles have a particle size of less than 800 μm, such as less than 600 μm, such as less than 500 μm, such as less than 400 μm, such as less than 200 μm, prior to step a) above.

In another embodiment, crystals of fumaric acid ester are sieved or milled such that 90% of the particles have a particle size in the range of 5-1000 μm, such as in the range of 10-900 μm, such as in the range of 20-800 μm, such as in the range of 30-750 μm, such as in the range of 40-600 μm, such as in the range of 50-500 μm, such as in the range of 100-400 μm, such as in the range of 200-300 μm, such as in the range of 300-600 μm, such as in the range of 300-400 μm, such as in the range of 400-600 μm or such as in the range of 500-600 μm, prior to step a) above.

In another embodiment, the mean particle size of the active pharmaceutical ingredient (the fumaric acid ester(s)) is in the range of 5-1000 μm, such as in the range of 10-900 μm, such as in the range of 20-800 μm, such as in the range of 30-750 μm, such as in the range of 40-600 μm, such as in the range of 50-500 μm, such as in the range of 100-400 μm, such as in the range of 200-300 μm, such as in the range of 300-600 μm, such as in the range of 300-400 μm, such as in the range of 400-600 μm or such as in the range of 500-600 μm, prior to step a) above.

In another embodiment, the particle size distribution of the active pharmaceutical ingredient (the fumaric acid ester(s)) is such that 0-5% of the particles have a particle size>500 μm and 45-53% of the particles have a particle size>250 μm, prior to step a) above. In a variant hereof 7-15% of the particles have a particle size<100 μm, prior to step a) above.

In another embodiment, the particle size distribution of the active pharmaceutical ingredient (the fumaric acid ester(s)) is such that 0-7% of the particles have a particle size>500 μm and 42-59% of the particles have a particle size>250 μm, prior to step a) above. In a variant hereof 3-12% of the particles have a particle size<100 μm, prior to step a) above.

In another embodiment, the particle size distribution of the active pharmaceutical ingredient (the fumaric acid ester(s)) is such that 0-10% of the particles have a particle size>500 μm and 40-65% of the particles have a particle size>250 μm, prior to step a) above. In a variant hereof 2-10% of the particles have a particle size<100 μm, prior to step a) above.

In an embodiment of the invention the mean particle size of the active pharmaceutical ingredient (the fumaric acid ester(s)) is reduced, e.g. by sieving or milling, wherein said sieving or milling is performed producing a minimum amount of heat. Thereby any sublimation of the active pharmaceutical ingredient is minimised or reduced and an energy-efficient process is obtained, mitigating loss of API, thus reducing cost as well as improving environmental and workers' safety. The sieving or milling may take place as a single sieving or milling step or may optionally be repeated several times to obtain the required particle distribution. In one embodiment of the invention, the sieving or milling takes place as a two-step process. In one embodiment of the invention, where the sieving or milling is performed as several steps an agent for reducing agglomeration is added in between the steps.

Without being bound by theory the present inventors believe that the active pharmaceutical ingredient (the fumaric acid ester(s)) having a particle size distribution in the above ranges results in a slower in vitro dissolution and thereby enables the use of a lower amount of rate-controlling agent compared to a formulation having a particle size distribution with a higher particle size e.g. such that more than 10% of the particles have a particle size>500 μm and/or more than 65% of the particles have a particle size>250 μm.

In one aspect, the lower amount of rate-controlling agent enables manufacture of a tablet with a high drug load such as at least 40%, 45%, 50%, 55%, or 60% active pharmaceutical ingredient based on the total tablet weight.

In an embodiment of the invention step b) is performed in a fluid bed granulator.

Another aspect of the invention is a method for preparing the formulation according to the invention, comprising the steps of:
a) Dissolving (or suspending) a rate-controlling agent in the form of a polymeric matrix material in water to obtain an aqueous suspension thereof;
b) Spraying said aqueous suspension on granules of a fumaric acid ester for a period of time sufficient to obtain a uniform coating thereon;
c) Drying the granules obtained;
d) Optionally sieving or milling said granules;
e) Blending of any pharmaceutically acceptable excipients and additives in a manner known per se to obtain a tablet formulation;
f) Optionally film and/or enteric coating of said tablet formulation in a manner known per se;
wherein any of or all of the above steps are performed at a temperature to allow a product temperature not exceeding 45° C. In an embodiment of the invention any of or all of the above steps are performed at a temperature to allow a product temperature not exceeding 40° C., such as not exceeding 35° C., such as not exceeding 30° C. Thereby any sublimation of the active pharmaceutical ingredient is minimised or reduced and an energy-efficient process is obtained, mitigating loss of API, thus reducing cost as well as improving environmental and workers' safety.

In an embodiment of the invention the fumaric acid ester is micronized to obtain a particle size, wherein at least 90% of the particles have a particle size of at most 50 μm, such as at most 30 μm, such as at most 10 μm, prior to step b) above.

In another embodiment, the mean particle size of the active pharmaceutical ingredient (the fumaric acid ester(s)) is reduced, e.g. by sieving or milling, wherein at least 90% of the particles have a particle size of at most 800 μm, such as at most 600 μm, such as at most 500 μm, such as at most 400 μm, such as at most 200 μm, prior to step b) above.

In an embodiment of the invention step b) is performed in a fluid bed granulator.

Another embodiment of the invention is a method for preparing the formulation according to the invention, comprising the steps of:
a) Optionally sieving or milling crystals of fumaric acid ester;
b) Blending of said crystals of fumaric acid ester, optionally a rate-controlling agent in the form of a polymeric matrix material, and any pharmaceutically acceptable excipients and additives by direct compression to obtain a tablet formulation;
c) Optionally film and/or enteric coating of said tablet formulation in a manner known per se;
wherein any of or all of the above steps are performed at a temperature to allow a product temperature not exceeding 45° C. In an embodiment of the invention any of or all of the above steps are performed at a temperature to allow a product temperature not exceeding 40° C., such as not exceeding 35° C., such as not exceeding 30° C. Thereby any sublimation of the active pharmaceutical ingredient is minimised or reduced and an energy-efficient process is obtained, mitigating loss of API, thus reducing cost as well as improving environmental and workers' safety.

Another embodiment of the invention is a method for preparing the formulation according to the invention, comprising the steps of:
a) Optionally sieving or milling crystals of fumaric acid ester;
b) Blending said crystals of fumaric acid ester with any pharmaceutically acceptable excipients and optionally a rate-controlling agent in the form of a polymeric matrix material in a manner known per se to obtain a tablet formulation;
c) Roller compaction of this blend and sieving/milling thereof in order to obtain granules;
d) Admixing of any further pharmaceutically acceptable excipients to the granules to obtain a final mix ready for tabletting;
e) Compression to tablets;
f) Optionally film and/or enteric coating of said tablets.

In an embodiment of the invention the fumaric acid ester is preblended with one or more pharmaceutically acceptable excipients before step a) above.

The stability of the formulations according to the invention may be determined by measuring the initial in vitro dissolution profile of the tablets and the in vitro dissolution profile after different periods of storage and comparing the in vitro dissolution profiles obtained. In an embodiment of the invention the tablets are stable for at least 6 months, such as at least 9 months, such as at least 12 months, such as at least 18 months, such as at least 24 months. The stability of the formulations according to the invention may also be determined by standardized methods for measuring any changes in for example assay, colour or degradation products.

In an embodiment of the invention, stability of a formulation can be defined by objective criteria, such as e.g. a certain maximum change of the amount of API released at a predetermined time point during a standardized in vitro dissolution test, when comparing the initial testing time point to testing at a later point in time. In an embodiment of the invention, the amount of the API released from the formulation stored under ICH conditions (such as 25 degrees C./60% RH, such as 30 degrees C./65% RH, such as 40 degrees C./75% RH) for a certain period of time (such as at least 1 month, such as at least 3 months, such as at least 6 months, such as at least 9 months, such as at least 12 months) c.f. the initial time point (time=0, set down of stability testing)—when subjected to an in vitro dissolution test employing 0.1 N hydrochloric acid as dissolution medium during the first 2 hours of the test and then 0.05 M phosphate buffer pH 6.8 as dissolution medium—is as follows:

1 hour after start of the test, a difference of less than 10 percentage points, such as less than 9 percentage points, such as less than 8 percentage points, such as less than 6 percentage points, such as less than 4 percentage points, such as less than 2 percentage points, such as less than 1 percentage point in the amount of the active pharmaceutical ingredient released from the formulation is observed, and/or 2 hours after start of the test, a difference of less than 10 percentage points, such as less than 9 percentage points, such as less than 8 percentage points, such as less than 6 percentage points, such as less than 4 percentage points, such as less than 2 percentage points, such as less than 1 percentage point in the amount of the active pharmaceutical ingredient released from the formulation is observed, and/or 3 hours after start of the test, a difference of less than 10 percentage points, such as less than 9 percentage points, such as less than 8 percentage points, such as less than 6 percentage points, such as less than 4 percentage points, such as less than 2 percentage points, such as less than 1 percentage point in the amount of the active pharmaceutical ingredient released from the formulation is observed, and/or 4 hours after start of the test, a difference of less than 10 percentage points, such as less than 9 percentage points, such as less than 8 percentage points, such as less than 6 percentage points, such as less than 4 percentage points, such as less than 2 percentage points, such as less than 1 percentage point in the amount of the active pharmaceutical ingredient released from the formulation is observed, and/or 5 hours after start of the test, a difference of less than 10 percentage points, such as less than 9 percentage points, such as less than 8 percentage points, such as less than 6 percentage points, such as less than 4 percentage points, such as less than 2 percentage points, such as less than 1 percentage point in the amount of the active pharmaceutical ingredient released from the formulation is observed.

In an embodiment the pharmaceutical formulation according to the invention is for use for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

An embodiment is the use of a pharmaceutical formulation according to the invention for the preparation of a medicament for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

Another embodiment of the invention is a method of treating psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare, which method comprises administering orally to a patient in need thereof an effective dosage of a pharmaceutical formulation according to the invention.

In an embodiment of the invention the formulation according to the invention is for use in the treatment of psoriasis.

In an embodiment of the invention the formulation according to the invention is for use in the treatment of psoriatic arthritis.

In an embodiment of the invention the formulation according to the invention is for use in the treatment of multiple sclerosis or relapsing-remitting multiple sclerosis.

In an embodiment of the invention the formulation according to the invention is for use in the treatment of rheumatoid arthritis.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All publications mentioned herein are incorporated herein by reference to disclose and describe the methods and/or materials in connection with which the publications are cited. It must be noted that as used herein and in the appended claims, the singular forms "a", "an", and "the" include plural referents unless the context clearly dictates otherwise. The patents and publications discussed herein are provided solely for their disclosure prior to the filing date of the present application. Nothing herein is to be construed as an admission that the present invention is not entitled to antedate such patent or publication by virtue of prior invention. Further, the dates of publication provided may be different from the actual publication dates which may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. The figures shown herein are not necessarily drawn to scale, with some components and features being exaggerated for clarity.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLES

During the carrying out of all the following steps in examples 1-24 and 26-42 necessary precautions are taken (protective clothing with external air supply, double gloves, arm covers, breathing mask, etc.).

Example 1

Preparation of Core Tablets 540.5 g of micronized dimethyl fumarate (mean particle size 10 μm) and 31.5 g hydroxypropyl cellulose HPC-SL was suspended in 1716 g purified water. The suspension was sprayed over app. 2 hours onto 405.5 g Granulac®140 lactose placed in the basket of a fluid bed granulator. The granules were dried for 5 minutes. A seal coat was applied by spraying a solution of 22.5 g HPC-SL in 2265.5 g purified water over app. 2 hours. The product temperature never exceeded 35° C. Different batches were blended and sieved through a 1.1 mm sieve.

183.3 g of the dried, sieved granules were blended with 58.7 g spray-dried lactose (FlowLac® 100) with a barrel blender at 30 rpm over 15 minutes. Finally, 2.4 g magnesium stearate was added and blended over additional 10 minutes at 30 rpm. The final blend was pressed into biconvex tablets with a diameter of 10 mm and a weight of 375 mg.

Example 2

Preparation of Core Tablets 540.5 g of non-micronized dimethyl fumarate and 405.5 g Granulac® 140 were placed in the basket of a fluid bed granulator. 62.1 g hydroxypropyl cellulose HPC-SL was dissolved by stirring in 3043 g purified water and sprayed on DMF over 2.5 hours. The granules were dried over 4 minutes at 29° C. and sieved through a 1.1 mm sieve. The product temperature never exceeded 30° C.

135 g of the dried granules were blended with 30.4 g spray-dried lactose (FlowLac® 100), 24.4 g HPC-SL and 0.3 g Aerosil with a barrel blender at 30 rpm over 15 minutes. Finally, 1.8 g magnesium stearate was added and blended over additional 10 minutes at 30 rpm. The final blend was pressed into biconvex tablets with a diameter of 10 mm and a weight of 315.5 mg.

Example 3

Preparation of Core Tablets 621.5 g of non-micronized dimethyl fumarate (mean particle size 500 μm) was suspended in 1793.5 g purified water and stirred with an Ultra-turrax for 5 hours to reduced particle size. Then 36.2 g hydroxypropyl cellulose HPC-SL was added. The suspension was sprayed over app. 2 hours onto 405.5 g Granulac® 140 placed in the basket of a fluid bed granulator. The granules were dried for 5 minutes. Hereafter a seal coat prepared from 26.3 g HPC-SL in 2605 g purified water was applied by spraying the solution over app. 2 hours onto the granules. The product temperature never exceeded 30° C.

183.3 g of the dried granules were blended with 58.7 g spray-dried lactose (FlowLac1® 100) and 0.5 g Aerosil with a barrel blender at 30 rpm over 15 minutes. Finally, 2.2 g magnesium stearate was added and blended over additional 10 minutes at 30 rpm. The final blend was pressed into biconvex tablets with a diameter of 10 mm and a weight of 375.4 mg.

Example 4

Preparation of Core Tablets 1200 g of non-micronized dimethyl fumarate was placed in the basket of a fluid bed granulator. 75 g hydroxypropyl cellulose HPC-SL was dissolved by stirring in 2925 g purified water and sprayed on DMF over app. 2.5 hours until 70 g HPC was sprayed. The granules were dried over 4 minutes at 29° C. and sieved through a 1.1 mm sieve. The product temperature never exceeded 30° C.

378.2 g of the dried granules were blended with 400.6 g spray-dried lactose (FlowLac® 100), 14.6 g HPC-SL and 0.9 g Aerosil with a barrel blender at 30 rpm over 15 minutes. Finally, 5.8 g magnesium stearate was added and blended over additional 10 minutes at 30 rpm. The final blend was pressed into biconvex tablets with a diameter of 8 mm and a weight of 275 mg.

Example 5

Film coating of core tablets according to example 4
Film Coating:

For film coating of 800 g core tablets a 15% suspension of Opadry was prepared by adding 36 g Opadry to 204 g purified water. App. 66% of this suspension was sprayed onto the core tablets over 35 minutes in a fluid bed chamber. The product temperature never exceeded 40° C. The coating process was followed by a drying period of 16 minutes at 30° C.

Example 6

Film and enteric coating of core tablets according to example 4
Film Coating

Film coating was done with 800 g core tablets. A 15% suspension of Opadry was prepared by adding 18 g Opadry to 102 g purified water. App. 66% of this suspension was sprayed onto the core tablets over 20 minutes in a fluid bed chamber. The product temperature never exceeded 40° C. The coating process was followed by a drying period of 9 minutes at 30° C.

Enteric Coating 1 kg gastric acid-resistant coating fluid was prepared by heating 350 ml purified water to 70-80° C., adding 20 g triethyl citrate, 3 g glyceryl monostearate (Cutina GMS V), 1 g Tween 80 and stirring with the UltraTurrax for 10 minutes to achieve a homogenous mixture. 427.8 g purified water was added and the mixture was stirred with a propeller stirrer until the emulsion had reached room temperature. This emulsion was then added slowly to 210 g of a Eudragit L30 D 55 dispersion. Approximately 66% of the resulting gastric acid-resistant coating fluid was sprayed on 780 g film coated tablets in a fluid bed chamber at a temperature of 30° C. over app. 2.5 hours. A drying period at 30° C. for 30 minutes and a curing period at 35° C. for additional 30 minutes followed.

Example 7

Enteric coating of core tablets according to example 4
Enteric Coating
1 kg gastric acid-resistant coating fluid was prepared and sprayed on core tablets as disclosed in example 6.

Example 8

Granules were prepared as disclosed in example 4.
416 g of the dried granules were blended with 360.8 g spray-dried lactose (FlowLac® 100), 16 g HPC-SL and 1 g Aerosil with a barrel blender at 30 rpm over 15 minutes. Finally, 6.4 g magnesium stearate was added and blended over additional 10 minutes at 30 rpm. The final blend was pressed into biconvex tablets with a diameter of 8 mm and a weight of 250 mg.

Example 9

Film coating of core tablets according to example 8
Film Coating
Film coating was carried out as disclosed in example 5.

Example 10

Film and enteric coating of core tablets according to example 8
Film Coating
Film coating was done with 800 g core tablets as disclosed in example 6.
Enteric Coating
1 kg gastric acid-resistant coating fluid was prepared and applied as disclosed in example 6.

Example 11

Granules were prepared as disclosed in example 4.
404.5 g of the dried granules are blended with 272.9 g spray dried lactose (FlowLac 100®), 15.5 g HPC-SL and 0.9 g Aerosil with a barrel blender at 30 rpm over 15 minutes. Finally, 6.2 g Magnesium stearate is added and blended over additional 10 minutes at 30 rpm. The final blend is pressed into biconvex tablets with a diameter of 8 mm and a weight of 225 mg.

Example 12

Film coating of core tablets is performed according to example 11
Film Coating
For film coating 800 g core tablets are coated as disclosed in example 5. To have 800 g tablets available for coating active tablets are blended with colored placebo.

Example 13

Film and enteric coating of core tablets according to example 11
Film Coating
Film coating was done with 800 g core tablets as disclosed in example 5. To have 800 g tablets available for coating active tablets were blended with colored placebo.
Enteric Coating
1 kg gastric acid-resistant coating fluid was prepared as applied as disclosed in example 6.

Example 14

Granules were prepared as in example 4.
130 g of the dried granules were blended with 52.7 g spray-dried lactose (FlowLac® 100), 40 g HPC-SL and 0.3 g Aerosil with a barrel blender at 30 rpm over 15 minutes. Finally, 2.0 g magnesium stearate was added and blended over additional 10 minutes at 30 rpm. The final blend was pressed into biconvex tablets with a diameter of 8 mm and a weight of 225 mg.

Example 15

Film coating of core tablets according to example 14
Film Coating
For film coating 800 g tablets were coated as disclosed in example 5. To have 800 g tablets available for coating active tablets were blended with colored placebo.

Example 16

Film and enteric coating of core tablets according to example 14
Film Coating
Film coating was done with 800 g core tablets. Therefore the API containing tablets were blended with colored placebo to obtain the required amount. A 15% suspension of Opadry was prepared and applied as disclosed in example 6.
Enteric Coating
1 kg gastric acid-resistant coating fluid was prepared and applied as disclosed in example 6.
The dissolution profile of film and enteric coated tablets according to this example was obtained in accordance with a United States Pharmacopeia (USP) in vitro test. The test was carried out at 37° C. using a paddle dissolution apparatus at 100 rpm employing 0.1 N hydrochloric acid as dissolution medium during the first 2 hours of the test and then followed by 0.05 M phosphate buffer pH 6.8 as dissolution medium for the remaining test period. The result appears from FIG. 1.

Example 17

1.2 kg dimethyl fumarate was sieved through a 700 μm sieve and placed in the basket of a fluid bed granulator. 70.6 g polymer hydroxypropyl cellulose HPC-SL was dissolved by stirring in 2753 g purified water and sprayed on the DMF over 2.5 to 3 hours. The granules were dried for 3 minutes at 29° C. Several batches were blended and sieved through a 800 μm sieve.
1730.7 g of the dried and additional through 500 μm sieved granules were blended with 781.3 g granulated lactose (Tablettose® 100), 66.7 g HPC-SL and a pre-blend of Aerosil® and Tablettose® with a barrel blender at 20 rpm over 15 minutes. The pre-blend was prepared in a polyethylene bag of 4 g colloidal silicic acid (Aerosil®) and 390.6 g Tablettose® and sieved through 500 μm. Finally, 26.7 g magnesium stearate was added. The final blend was pressed into biconvex tablets with a diameter of 8 mm and a weight of 225 mg.

Example 18

Film and enteric coating of core tablets according to example 17

Film Coating

For film coating of 800 g core tablets a 15% suspension of Opadry was prepared by adding 18 g Opadry to 102 g purified water. App. 66% of this suspension was sprayed onto the core tablets over 20 minutes in a fluid bed chamber. The product temperature never exceeded 40° C. The coating process was followed by a drying period of 9 minutes at 30° C.

Enteric Coating 1 kg gastric acid-resistant coating fluid was prepared by heating 350 ml purified water to 70-80° C., adding 9.5 g triethyl citrate, 1.9 g glyceryl monostearate (Cutina GMS V), 0.7 g Tween 80 and stirring with the UltraTurrax for 10 minutes to achieve a homogenous mixture. 427.8 g purified water was added and the mixture was stirred with a propeller stirrer until the emulsion had reached room temperature. This emulsion was then added slowly to 210 g of a Eudragit® L30 D 55 dispersion. Approximately 66% of the resulting gastric acid-resistant coating fluid was sprayed on 780 g film-coated tablets in a fluid bed chamber.

The dissolution profile of film and enteric coated tablets according to this example was obtained in accordance with an in vitro dissolution test as described in example 16 employing 0.1 N hydrochloric acid as dissolution medium during the first 2 hours of the test and then 0.05 M phosphate buffer pH 6.8 as dissolution medium appears from FIG. 1.

Example 19

1.2 kg dimethyl fumarate was sieved through a 700 μm sieve and placed in the basket of a fluid bed granulator. 70.6 g hydroxypropyl cellulose HPC-SL was dissolved by stirring in 2753 g purified water and sprayed on the DMF over 2.5 to 3 hours. The granules were dried for 3 minutes at 29° C. and sieved through a 500 μm sieve.

964 g of the dried, sieved granules were blended with 565.5 g granulated lactose (Tablettose® 100), 37.4 g HPC-SL and a pre-blend of Aerosil® and Tablettose® with a barrel blender at 20 rpm over 15 minutes. The pre-blend was prepared in a polyethylene bag of 2.3 g colloidal silicic acid (Aerosil®) and 282.7 g Tablettose® and sieved through 500 μm as well. Finally, 14.9 g magnesium stearate was added. The final blend was pressed into biconvex tablets with a diameter of 8 mm and a weight of 250 mg.

Example 20

Film and enteric coating of core tablets according to example 19
Film Coating

For film coating of 800 g core tablets a 15% suspension of Opadry is prepared and applied as disclosed in example 18.

Enteric Coating 1 kg gastric acid-resistant coating fluid was prepared by heating 350 ml purified water to 70-80° C., adding 9.5 g triethyl citrate, 1.9 g glyceryl monostearate (Cutina GMS V), 0.7 g Tween 80 and stirring with the UltraTurrax for 10 minutes to achieve a homogenous mixture. 427.8 g purified water was added and the mixture was stirred with a propeller stirrer until the emulsion had reached room temperature. This emulsion was then added slowly to 210 g of a Eudragit® L30 D 55 dispersion. Approximately 66% of the resulting gastric acid-resistant coating fluid was sprayed on 780 g film coated tablets in a fluid bed chamber at a temperature of 30° C. over app. 2.5 hours. A drying period at 30° C. for 30 minutes and a curing period at 35° C. for additional 30 minutes followed.

The dissolution profile of film and enteric coated tablets according to this example was obtained in accordance with an in vitro dissolution test as described in example 16 employing 0.1 N hydrochloric acid as dissolution medium during the first 2 hours of the test and then 0.05 M phosphate buffer pH 6.8 as dissolution medium appears from FIG. 1.

Example 21

1.2 kg dimethyl fumarate was sieved through a 700 μm sieve and placed in the basket of a fluid bed granulator. 70.6 g hydroxypropyl cellulose HPC-SL was dissolved by stirring in 2753 g purified water and sprayed on the DMF over 2.5 to 3 hours. The granules were dried for 3 minutes at 29° C. Several batches were blended and sieved through 800 μm.

1416 g of the dried and additional through 500 μm sieved granules were blended with 1002.9 g granulated lactose (Tablettose® 100), 54.6 g HPC-SL and a pre-blend of Aerosil® and Tablettose® with a barrel blender at 20 rpm over 15 minutes. The pre-blend was prepared in a polyethylene bag of 3.3 g colloidal silicic acid (Aerosil®) and 501.4 g Tablettose® and sieved through 500 μm. Finally, 21.8 g magnesium stearate was added. The final blend was pressed into biconvex tablets with a diameter of 8 mm and a weight of 275 mg.

Example 22

Film and enteric coating of core tablets according to example 21
Film Coating

For film coating of 800 g core tablets a 15% suspension of Opadry was prepared and applied as disclosed in example 18.

Enteric Coating:

1 kg gastric acid-resistant coating fluid was prepared by heating 350 ml purified water to 70-80° C., adding 9.5 g triethyl citrate, 1.9 g glyceryl monostearate (Cutina GMS V), 0.7 g Tween 80 and stirring with the UltraTurrax for 10 minutes to achieve a homogenous mixture. 427.8 g purified water was added and the mixture was stirred with a propeller stirrer until the emulsion had reached room temperature. This emulsion was then added slowly to 210 g of a Eudragit® L30 D 55 dispersion. Approximately 66% of the resulting gastric acid-resistant coating fluid was sprayed on 780 g film coated tablets in a fluid bed chamber at a temperature of 30° C. over app. 2.5 hours. A drying period at 30° C. for 30 minutes and a curing period at 35° C. for additional 30 minutes followed.

The dissolution profile of film and enteric coated tablets according to this example was obtained in accordance with an in vitro dissolution test as described in example 16 employing 0.1 N hydrochloric acid as dissolution medium during the first 2 hours of the test and then 0.05 M phosphate buffer pH 6.8 as dissolution medium appears from FIG. 1.

Example 23

Film coating of core tablets according to example 18
Film Coating

For film coating of 800 g core tablets a 15% suspension of Opadry was prepared by adding 36 g Opadry to 204 g purified water. App. 66% of this suspension was sprayed onto the core tablets over 35 minutes in a fluid bed chamber. The product temperature never exceeded 40° C. The coating process was followed by a drying period of 16 minutes at 30° C.

The dissolution profile of film coated tablets according to this example was subjected to an in vitro dissolution test employing 0.1 N hydrochloric acid as dissolution medium during the first 2 hours of the test and then 0.05 M phosphate buffer pH 6.8 as dissolution medium appears from FIG. 2.

Example 24

18 g of pure DMF (particle size 250-500 µm) were blended with 6.3 g HPC-SL, 9.1 g spray dried lactose (FlowLac® 100) and 0.045 g Aerosil. Finally, 0.3 g magnesium stearate was added and blended. The final blend was pressed into biconvex tablets with a diameter of 8 mm and a weight of 225 mg.

Example 25

The study was a single center study, following an open-label, randomized, crossover design to investigate the plasma concentrations, pharmacokinetics, safety and tolerability of pharmaceutical formulations according to the invention c.f. the marketed formulation Fumaderm® as reference. The tablets were administered as a single oral dose of 240 mg (2 tablets containing 120 mg each) in each treatment period according to randomization to 20 healthy, male Caucasian subjects. The study was divided into four treatment periods (Treatment Period 1, 2, 3 and 4), which were separated by a wash-out phase of at least 7 days.

Subjects were screened for eligibility at least 21 to 2 days before first administration including: check of inclusion/exclusion criteria; demographic data (including age, body height, body weight, body mass index (BMI), and ethnic origin); physical examination; complete medical history; 12-lead electrocardiogram (ECG); vital signs (blood pressure (BP), pulse rate (PR), and body temperature (BT)); clinical laboratory parameters (hematology, serum biochemistry, and urinalysis); documentation of concomitant illness and medication.

At each of the four treatment periods, subjects came to the Study Site in the evening of Day-1 and remained there until the 24-hour blood sample for PK analysis was drawn and all safety measurements were performed (=morning of Day 2).

The subjects fasted overnight. A single oral dose (of two tablets) of one of the formulations according to the invention (Examples 18, 20 or 22), or two enteric-coated tablets of the reference medication Fumaderm® each containing 120 mg dimethyl fumarate (total dose 240 mg dimethyl fumarate) were administered on Day 1 (according to randomization). Administration was done to subjects who were in fasting condition together with 240 ml tap water. Between each administration, a wash-out interval of at least 7 days was maintained.

The following assessments/measurements were performed:

Blood sampling was performed for the determination of plasma concentrations and PK-parameters prior to, and at pre-scheduled times post dosing.

Adverse events were documented in detail throughout the study.

Urine was collected prior to and at pre-scheduled times post dosing.

A follow-up examination was performed at least 7 days after the last administration (Treatment Period 4), including: physical examination; vital signs (BP, PR, and BT); body weight; 12-lead ECG; clinical laboratory parameters (haematology, serum biochemistry, and urinalysis); documentation of concomitant medication and adverse events.

Example 26

Preparation of Core Tablets

Dimethyl fumarate was sieved through a hand screen of 500 µm.

29.3 g of sieved dimethyl fumarate, 2.93 g of HPC-SL, 22.17 g of granulated lactose (Tablettose® 100), 0.07 g of Aerosil® as well as 0.49 g of magnesium stearate were blended for 10 minutes. The blend was pressed into biconvex tablets with a diameter of 8 mm and a weight of 225 mg.

Example 27a

Preparation of Core Tablets

Dimethyl fumarate was sieved through a hand screen of 500 µm.

500 g of sieved dimethyl fumarate, 48 g of HPC-SL, 447 g of spray dried lactose (FlowLac® 100) and 1.2 g Aerosil® were blended with a barrel blender for 15 minutes at 20 rpm. Finally, 4 g of magnesium stearate was added and the mixture blended again for 10 min at 20 rpm. The blend was pressed into biconvex tablets with a diameter of 8 mm and a weight of 250 mg.

Enteric Coating

A gastric acid-resistant coating fluid was prepared by heating 247 g of purified water to 70-80° C., then 9 g of triethyl citrate, 1.8 g of glyceryl monostearate (Cutina GMS V), and 0.72 g of Tween 80 was added and stirred with the UltraTurrax for 10 minutes to achieve a homogenous mixture. 495 g of purified water was added and the mixture was stirred with a propeller stirrer until the emulsion had reached room temperature. This emulsion was then added slowly to 200 g of Eudragit L30 D 55 dispersion. The resulting gastric acid-resistant coating fluid was sprayed on the core tablets directly in a perforated drum coater. The amount of solution sprayed onto the tablets was 1.5% solids w/w resulting in a weight increase of the coated tablets compared to core tablets of 1%.

Example 27b

Preparation of core tablets was performed as described in Example 27a.

Enteric Coating

A gastric acid-resistant coating fluid was prepared by heating 247 g of purified water to 70-80° C., then 9 g of triethyl citrate, 1.8 g of glyceryl monostearate (Cutina GMS V), and 0.72 g of Tween 80 was added and stirred with the UltraTurrax for 10 minutes to achieve a homogenous mixture. 495 g of purified water was added and the mixture was stirred with a propeller stirrer until the emulsion had reached room temperature. This emulsion was then added slowly to 200 g of Eudragit L30 D 55 dispersion. The resulting gastric acid-resistant coating fluid was sprayed on the core tablets directly in a perforated drum coater. The amount of solution sprayed onto the tablets was 2.5% solids w/w resulting in a weight increase of the coated tablets compared to core tablets of 1.8%.

Example 28

Preparation of Core Tablets

Dimethyl fumarate was sieved through a hand screen of 500 µm.

500 g sieved dimethyl fumarate, 48 g of HPC-SL and 447 g of granulated lactose (Tablettose® 100) and 1.2 g Aerosil® were blended with a barrel blender for 15 minutes at 20 rpm. Finally, 4 g of magnesium stearate was added and the mixture blended again for 10 min at 20 rpm. The blend was pressed into biconvex tablets with a diameter of 8 mm and a weight of 250 mg.

Enteric Coating

A gastric acid-resistant coating fluid was prepared by heating 99 g of purified water to 70-80° C., then 10.1 g of triethyl citrate, 2.0 g of glyceryl monostearate (Cutina GMS V), and 0.8 g of Tween 80 was added and stirred with the UltraTurrax for 10 minutes to achieve a homogenous mixture. 198 g of purified water was added and the mixture was stirred with a propeller stirrer until the emulsion had reached room temperature. This emulsion was then added slowly to 224 g of Eudragit L30 D 55 dispersion. The resulting gastric acid-resistant coating fluid was sprayed on the core tablets directly in a perforated drum coater. The solution was sprayed to a weight increase of the core tablets of 3%.

Example 29a

Preparation of Core Tablets

Dimethyl fumarate was milled through 1143 µm and 610 µm screens.

500 g sieved dimethyl fumarate, 48 g of HPC-SL and 447 g of granulated lactose (Tablettose® 100) and 1.2 g of Aerosil® were blended with a barrel blender for 15 minutes at 20 rpm. Finally, 4 g of magnesium stearate was added and the mixture blended again for 10 min at 20 rpm. The blend was pressed into biconvex tablets with a diameter of 8 mm and a weight of 250 mg.
Enteric Coating A gastric acid-resistant coating fluid was prepared by heating 247 g of purified water to 70-80° C., then 9 g of triethyl citrate, 1.8 g of glyceryl monostearate (Cutina GMS V), and 0.72 g of Tween 80 was added and stirred with the UltraTurrax for 10 minutes to achieve a homogenous mixture. 495 g of purified water was added and the mixture was stirred with a propeller stirrer until the emulsion had reached room temperature. This emulsion was then added slowly to 200 g of Eudragit L30 D 55 dispersion. The resulting gastric acid-resistant coating fluid was sprayed on the core tablets directly in a perforated drum coater. The amount of Eudragit sprayed onto the tablets was 2.5% solids w/w resulting in a weight increase of the coated tablets compared to core tablets of 1.5%.

Example 29b

Preparation of core tablets was performed as described in Example 29a.
Enteric Coating A gastric acid-resistant coating fluid was prepared by heating 247 g of purified water to 70-80° C., then 9 g of triethyl citrate, 1.8 g of glyceryl monostearate (Cutina GMS V), and 0.72 g of Tween 80 was added and stirred with the UltraTurrax for 10 minutes to achieve a homogenous mixture. 495 g of purified water was added and the mixture was stirred with a propeller stirrer until the emulsion had reached room temperature. This emulsion was then added slowly to 200 g of Eudragit L30 D 55 dispersion. The resulting gastric acid-resistant coating fluid was sprayed on the core tablets directly in a perforated drum coater. The amount of Eudragit sprayed onto the tablets was 3.5% solids w/w resulting in a weight increase of the coated tablets compared to core tablets of 2%.

Example 30

Preparation of Core Tablets 2500 g of dimethyl fumarate was milled through 1575 µm and 813 µm screens. Before the second milling step 6 g of Aerosil® was added. The achieved particle size distribution was approx. 11%>500 µm, approx. 70%>250 µm and approx. 7%<100 µm. The mean particle size was 358 µm.

The milled material was blended further with 240 g of HPC-SL and 2714 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 275 mg. The core tablets were optionally enteric coated as described in example 33a.

Example 31

Preparation of Core Tablets 2500 g of dimethyl fumarate was milled through 1575 µm and 813 µm screens. Before the second milling step 6 g of Aerosil® was added. The achieved particle size distribution was approx. 3%>500 µm, approx. 65%>250 µm and approx. 6%<100 µm. The mean particle size was 290 µm.

The milled material was blended further with 240 g of HPC-SL and 2714 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 275 mg. The core tablets may be enteric coated as described in example 33a or b.

Example 32

Preparation of Core Tablets 2500 g of dimethyl fumarate was milled through 1575 µm and 813 µm screens. Before the second milling step 6 g of Aerosil® was added. The achieved particle size distribution was approx. 3%>500 µm, approx. 50%>250 µm and approx. 10%<100 µm. The mean particle size was 250 µm.

The milled material was blended further with 240 g of HPC-SL and 2714 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 275 mg. The core tablets were optionally enteric coated as described in example 33b.

Example 33a

Enteric Coating

A gastric acid-resistant coating fluid was prepared by heating 1193 g of purified water to 70-80° C., then 45 g of triethyl citrate, 13.5 g of glyceryl monostearate (Cutina GMS V), and 5.4 g of Tween 80 was added and stirred with the UltraTurrax for 10 minutes to achieve a homogenous mixture. 2385 g of purified water was added and the mixture was stirred with a propeller stirrer until the emulsion had reached room temperature. This emulsion was then added slowly to 1500 g of Eudragit L30 D 55 dispersion. The resulting gastric acid-resistant coating fluid was sprayed on the core tablets directly in a perforated drum coater. The amount of Eudragit sprayed onto the tablets was 3.0% w/w resulting in a weight increase of the coated tablets compared to core tablets of 2.5%.

Example 33b

Enteric Coating

A gastric acid-resistant coating fluid was prepared by heating 1193 g of purified water to 70-80° C., then 45 g of triethyl citrate, 13.5 g of glyceryl monostearate (Cutina GMS V), and 5.4 g of Tween 80 was added and stirred with the UltraTurrax for 10 minutes to achieve a homogenous mixture. 2385 g of purified water was added and the mixture was stirred with a propeller stirrer until the emulsion had reached room temperature. This emulsion was then added slowly to 1500 g of Eudragit L30 D 55 dispersion. The resulting gastric acid-resistant coating fluid was sprayed on the core tablets directly in a perforated drum coater. The amount of Eudragit sprayed onto the tablets was 3.5% resulting in a weight increase of the coated tablets compared to core tablets of 3%.

Example 34

Preparation of Core Tablets 2500 g of dimethyl fumarate was milled through 1575 μm and 813 μm screens. Before the second milling step 6 g Aerosil® was added. The achieved particle size distribution was 8%>500 μm, 80%>250 μm and 0%<100 μm. The mean particle size was 360 μm.

The milled material was blended further with 240 g of HPC-SL and 2234 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 250 mg. The core tablets may be enteric coated as described in example 33a or b.

Example 35

Preparation of Core Tablets 2500 g of dimethyl fumarate was milled through 1575 μm and 813 μm screens. Before the second milling step 6 g Aerosil® was added. The achieved particle size distribution was 6%>500 μm, 65%>250 μm and 6%<100 μm. The mean particle size was 305 μm.

The milled material was blended further with 240 g of HPC-SL and 2234 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 250 mg. The core tablets may be enteric coated as described in example 33a or b.

Example 36

Preparation of Core Tablets 2500 g of dimethyl fumarate was milled through 1575 μm and 813 μm screens. Before the second milling step 6 g Aerosil® was added. The achieved particle size distribution was 3%>500 μm, 63%>250 μm and 6%<100 μm. The mean particle size was 290 μm.

The milled material was blended further with 240 g of HPC-SL and 2234 g of granulated lactose (Tablettose® 100) with a barrel blender for 15 minutes at 20 rpm. Finally, 20 g of magnesium stearate was added and the mixture blended again for 10 min at 20 rpm. The blend was pressed into biconvex tablets with a diameter of 8 mm and a weight of 250 mg. The core tablets may be enteric coated as described in example 33a or b.

Example 37

Preparation of Core Tablets 2500 g of dimethyl fumarate is milled through 1575 μm and 813 μm screens. Before the second milling step 6 g of Aerosil® is added.

The milled material is blended further with 240 g of HPC-SL and 1714 g of granulated lactose (Tablettose® 100) with a barrel blender for 15 minutes at 20 rpm. Finally, 20 g of magnesium stearate is added and the mixture blended again for 10 min at 20 rpm. The blend is pressed into biconvex tablets with a diameter of 8 mm and a weight of 225 mg. The core tablets may be enteric coated as described in example 33a or b.

Example 38

2.500 g of DMF is milled through 1575 μm and 813 μm screens. 240 g of HPC-SL, 2.734 g of Tablettose 100 and 6 g of Aerosil is added and blended with the DMF. The blend is roller compacted and passed through a 1 mm screen to obtain granules. 20 g of magnesium stearate is admixed to obtain a final mix ready for tabletting. Said mix is compressed to tablets having a tablet weight of 275 mg. The core tablets may be enteric coated as described in example 33a or b.

Example 39

2.500 g of DMF is blended with 6 g of Aerosil and subsequently milled through 1575 μm and 813 μm screens. 240 g of HPC-SL and 2.734 g of Tablettose 100 is added and blended with the DMF and Aerosil. The blend is roller compacted and passed through a 1 mm screen to obtain granules. 20 g of magnesium stearate is admixed to obtain a final mix ready for tabletting. Said mix is compressed to tablets having a tablet weight of 275 mg. The core tablets may be enteric coated as described in example 33a or b.

Example 40

2000 g dimethyl fumarate was milled through 1575 μm and 813 μm screens. Before the second milling step 4.8 g of Aerosil® was added.

475.3 g of the milled material was blended further with 519.8 g of granulated lactose (Tablettose® 100) with a barrel blender for 15 minutes at 20 rpm. Finally, 3.8 g of magnesium stearate was added and the mixture was blended again for 10 min at 20 rpm. The blend was pressed into biconvex tablets with a diameter of 8 mm and a weight of 263 mg. The core tablets may be enteric coated as described in example 33a or b.

Example 41

2000 g dimethyl fumarate was milled through 1575 μm and 813 μm screens. Before the second milling step 4.8 g of Aerosil® was added.

468.2 g of the milled material was blended further with 15 g HPC-SL and 512 g of granulated lactose (Tablettose® 100) with a barrel blender for 15 minutes at 20 rpm. Finally, 3.7 g of magnesium stearate was added and the mixture was blended again for 10 min at 20 rpm. The blend was pressed into biconvex tablets with a diameter of 8 mm and a weight of 267 mg. The core tablets may be enteric coated as described in example 33a or b.

Example 42

2000 g dimethyl fumarate was milled through 1575 μm and 813 μm screens. Before the second milling step 4.8 g of Aerosil® was added.

500 g of the milled material was blended further with 32 g HPC-SL and 562.8 g of granulated lactose (Tablettose® 100) with a barrel blender for 15 minutes at 20 rpm. Finally, 4 g of magnesium stearate was added and the mixture was blended again for 10 min at 20 rpm. The blend was pressed into biconvex tablets with a diameter of 8 mm and a weight of 250 mg. The core tablets may be enteric coated as described in example 33a or b.

Example 43

A study as the one disclosed in example 25 was performed on tablets as disclosed in examples 18 and 22 and compared with corresponding data for the prior art formulation Fumaderm®. The results of the study are shown in Table I and Table II below.

TABLE I

Coefficients of variation in % (CV).

|  | Example 18 | Example 22 | Fumaderm ® |
|---|---|---|---|
| AUC | 22% | 18% | 38% |
| $C_{max}$ | 34% | 26% | 49% |

TABLE II

Summary Table: Percentage of subjects with adverse effects/side effects after administration of formulation according to examples 18 and 22, respectively, compared to administration of Fumaderm ®

| Adverse effect/ side effect | After administration of formulation acc. to ex 18. c.f. after administration of Fumaderm ® | After administration of formulation acc. to ex. 22 c.f. after administration of Fumaderm ® |
|---|---|---|
| Flushing | 35% | 65% |
| GI related adverse effects | 50% | 73% |
| Any adverse effect | 50% | 77% |

The above results of the clinical trial shows (Table II) that the tested formulations have a markedly reduced frequency of adverse effects combined with a lower variability (cf. Table I) compared to Fumaderm®. This example thus shows that the inventive formulations have an unexpectedly large reduction in variability in AUC and $C_{max}$ vis-à-vis the prior art Fumaderm® formulation.

The invention claimed is:

1. A pharmaceutical formulation in the form of an erosion matrix tablet comprising:
   a) a core tablet comprising
      i) 10% to 80% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
      ii) 1-50% by weight of one or more rate-controlling agents; and
   b) an enteric coating, wherein said enteric coating is applied at a level of 1.5-3.5% by weight of the core, wherein erosion of said erosion matrix permits controlled or sustained release of said active substance.

2. A pharmaceutical formulation according to claim 1 comprising:
   i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
   ii) 3-40% by weight of one or more rate-controlling agents.

3. A pharmaceutical formulation according to claim 1, wherein the erosion matrix is a monolithic erosion matrix.

4. The formulation according to claim 1, wherein the rate-controlling agent is a water-soluble polymer.

5. The formulation according to claim 1, wherein the rate-controlling agent is a cellulose polymer or a cellulose derivative or a mixture thereof.

6. The formulation according to claim 5, wherein the rate-controlling agent is selected from the group comprising hydroxypropyl cellulose, hydroxypropyl methyl cellulose (HPMC), methyl cellulose, carboxymethyl cellulose and mixtures thereof.

7. The formulation according to claim 6, wherein the rate-controlling agent is hydroxypropyl cellulose.

8. The formulation according to claim 1, further comprising a binder.

9. The formulation according to claim 8, wherein said binder is lactose.

10. The formulation according to claim 1 comprising:
    i) 40% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
    ii) 4-6% by weight of a rate-controlling agent;
    iii) 35-55% by weight of a binder.

11. The formulation according to claim 1 comprising:
    i) 30% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, as an active substance;
    ii) 3-6% by weight of a rate-controlling agent;
    iii) 35-65% by weight of a binder.

12. The formulation according to claim 1, wherein the release of the fumaric acid ester—when subjected to an in vitro dissolution test employing 0.1 N hydrochloric acid as dissolution medium during the first 2 hours of the test and then 0.05 M phosphate buffer pH 6.8 as dissolution medium—is as follows:
    within the first 2 hours after start of the test from about 0% w/w to about 50% w/w of the fumaric ester contained in the formulation is released, and/or
    within the first 3 hours after start of the test from about 20% w/w to about 75% w/w of the total amount of the fumaric acid ester contained in the formulation is released.

13. The formulation according to claim 1, wherein the fumaric acid ester is a mono-($C_1$-$C_5$) alkylester of fumaric acid that is present in the form of a pharmaceutically acceptable salt.

14. The formulation according to claim 1 comprising dimethylfumarate as the active substance.

15. The formulation according to claim 1 comprising:
    i) 40% to 55% by weight of dimethyl fumarate;
    ii) 4-6% by weight of hydroxypropyl cellulose;
    iii) 35-55% by weight of lactose.

16. The formulation according to claim 1 comprising:
  i) 30% to 60% by weight of dimethyl fumarate;
  ii) 3-6% by weight of hydroxypropyl cellulose;
  iii) 35-65% by weight of lactose.

17. A method for preparing the formulation according to claim 1 comprising the steps of:
  a) Dissolving or suspending a rate-controlling agent in the form of a polymeric matrix material in water to obtain an aqueous suspension thereof;
  b) Spraying said aqueous suspension on granules of a fumaric acid ester for a period of time sufficient to obtain a uniform coating thereon;
  c) Drying the granules obtained;
  d) Optionally sieving or milling said granules;
  e) Blending of any pharmaceutically acceptable excipients and additives in a manner known per se to obtain a tablet formulation;
  f) enteric coating of said tablet formulation in a manner known per se;
  wherein the above steps are performed at a temperature to allow a product temperature not exceeding 45° C.

18. A method for preparing the formulation according to claim 1 comprising the steps of:
  a) Optionally sieving or milling crystals of fumaric acid ester;
  b) Blending of said crystals of fumaric acid ester, a rate-controlling agent in the form of a polymeric matrix material, and any pharmaceutically acceptable excipients and additives by direct compression to obtain a tablet formulation;
  c) enteric coating of said tablet formulation in a manner known per se;
wherein the above steps are performed at a temperature to allow a product temperature not exceeding 45° C.

19. The method according to claim 18, wherein the crystals of fumaric acid ester are sieved or milled such that 90% of the particles have a particle size in the range of 5-1000 μm.

20. A pharmaceutical formulation according to claim 1 for use for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

21. A use of a pharmaceutical formulation according to claim 1 for the preparation of a medicament for the treatment of psoriasis, psoriatic arthritis, neurodermatitis, inflammatory bowel disease, such as Crohn's disease and ulcerative colitis, polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA), lupus nephritis, myasthenia gravis, uveitis, refractory uveitis, vernal conjunctivitis, pemphigus vulgaris, scleroderma, optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

* * * * *

UNITED STATES PATENT AND TRADEMARK OFFICE
CERTIFICATE OF CORRECTION

PATENT NO. : 8,906,420 B2  Page 1 of 1
APPLICATION NO. : 13/143498
DATED : December 9, 2014
INVENTOR(S) : Henrik Nilsson et al.

It is certified that error appears in the above-identified patent and that said Letters Patent is hereby corrected as shown below:

On the Title Page

Page 1, item 30, under Foreign Application Priority Data, replace "2009 00034" with --PA 2009 00034--.

Page 2, item 56, under FOREIGN PATENT DOCUMENTS, insert --WO WO-2004/024138 A1 3/2004--.

Page 5, item 56, under OTHER PUBLICATIONS, in Bauer, replace "and" with --und--;

in Bauer, replace "überzogene" with --Überzogene--;

in "Aqueous," replace "EUDRAGI®" with --EUDRAGIT®--;

in "New Formulation," replace "EUDRAGI®" with --EUDRAGIT®--;

in "EUDRAGI®," replace "EUDRAGI®" with --EUDRAGIT®--.

In the Specification

Column 10, Line 53, replace "i.e. AUC" with --i.e. AUC%.--;

Column 30, Line 64, replace "$M_t = M_0 + k_H *^{1/2}$" with --$M_t = M_0 + k_H * t^{1/2}$--.

In the Claims

Column 54, Line 18, replace "claim 1" with --claim 4--.

Signed and Sealed this
Eighth Day of September, 2015

Michelle K. Lee
*Director of the United States Patent and Trademark Office*